United States Patent
Asahina et al.

(10) Patent No.: US 10,413,744 B2
(45) Date of Patent: Sep. 17, 2019

(54) TRANSCRANIAL MAGNETIC STIMULATION SYSTEM

(71) Applicant: Teijin Pharma Limited, Tokyo (JP)

(72) Inventors: Atsushi Asahina, Tokyo (JP); Kenji Tojo, Tokyo (JP); Rei Tamiya, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 252 days.

(21) Appl. No.: 15/517,272

(22) PCT Filed: Aug. 31, 2015

(86) PCT No.: PCT/JP2015/074583
§ 371 (c)(1),
(2) Date: Apr. 6, 2017

(87) PCT Pub. No.: WO2016/056327
PCT Pub. Date: Apr. 14, 2016

(65) Prior Publication Data
US 2017/0296838 A1    Oct. 19, 2017

(30) Foreign Application Priority Data

Oct. 7, 2014  (JP) .................................. 2014-206625

(51) Int. Cl.
*A61N 2/00*    (2006.01)
*A61N 2/02*    (2006.01)
(Continued)

(52) U.S. Cl.
CPC .............. *A61N 2/006* (2013.01); *A61B 90/30* (2016.02); *A61G 13/121* (2013.01);
(Continued)

(58) Field of Classification Search
CPC .................................................. A61N 2/00–12
See application file for complete search history.

(56) References Cited

U.S. PATENT DOCUMENTS

2003/0073899 A1    4/2003  Ruohonen et al.
2005/0234286 A1   10/2005  Riehl et al.
(Continued)

FOREIGN PATENT DOCUMENTS

EP    0672389 A2    9/1995
EP    2772282 A1    9/2014
(Continued)

OTHER PUBLICATIONS

Communication dated Aug. 31, 2017, from the European Patent Office in counterpart European application No. 15849495.5.
(Continued)

*Primary Examiner* — Thaddeus B Cox
(74) *Attorney, Agent, or Firm* — Sughrue Mion, PLLC

(57) ABSTRACT

The purpose of the invention is to provide a transcranial magnetic stimulation system capable of guiding a patient into an optimum posture for treatment. The system 1 of the invention includes an optical device 502 for projecting a light spot 805 to a head of a patient and detecting a reflection light of the light spot; a memory means 71 for memorizing information included in the reflection light detected by the optical device as a reference information when the projected light spot on the patient overlaps a marking (800) provided on the patient; a calculation means 72 for using the reference information memorized in the memory means and a comparison information included in the reflection light of the light spot to calculate an overlap ratio between the marking and the light spot corresponding to the comparison information; and a display means 504 for displaying the overlap ratio.

13 Claims, 24 Drawing Sheets

(51) Int. Cl.
- *A61G 13/12* (2006.01)
- *A61G 15/12* (2006.01)
- *A61B 90/30* (2016.01)
- *A61N 1/00* (2006.01)
- *A61B 90/00* (2016.01)

(52) U.S. Cl.
CPC ............ *A61G 15/125* (2013.01); *A61N 2/00* (2013.01); *A61N 2/02* (2013.01); *A61B 2090/363* (2016.02); *A61B 2090/3937* (2016.02); *A61G 2210/50* (2013.01); *A61N 1/00* (2013.01)

(56) References Cited

U.S. PATENT DOCUMENTS

| | | |
|---|---|---|
| 2009/0216067 A1 | 8/2009 | Lebosse et al. |
| 2009/0227830 A1* | 9/2009 | Pillutla ............... A61N 2/02 600/13 |
| 2014/0179981 A1 | 6/2014 | Katz et al. |
| 2015/0038768 A1 | 2/2015 | Saitoh et al. |

FOREIGN PATENT DOCUMENTS

| | | |
|---|---|---|
| JP | 2003-180649 A | 7/2003 |
| JP | 2006-320425 A | 11/2006 |
| JP | 2008-528108 A | 7/2008 |
| JP | 2010-503439 A | 2/2010 |
| JP | 5453325 B2 | 3/2014 |
| WO | 2006/078727 A2 | 7/2006 |
| WO | 2008/001003 A2 | 1/2008 |
| WO | 2008/031847 A1 | 3/2008 |
| WO | 2009/114526 A1 | 9/2009 |
| WO | 2013/062022 A1 | 5/2013 |

OTHER PUBLICATIONS

Translation of the International Preliminary Report on Patentability and the Written Opinion, dated Apr. 20, 2017, from the International Bureau in counterpart International application No. PCT/JP2015/074583.

International Search Report of PCT/JP2015/074583 dated Nov. 24, 2015.

* cited by examiner

TRANSCRANIAL MAGNETIC STIMULATION SYSTEM

CROSS REFERENCE TO RELATED APPLICATIONS

This application is a National Stage of International Application No. PCT/JP2015/074583 filed Aug. 31, 2015, claiming priority based on Japanese Patent Application No. 2014-206625 filed Oct. 7, 2014, the contents of all of which are incorporated herein by reference in their entirety.

TECHNICAL FIELD

The invention relates to a transcranial magnetic stimulation system for use in the transcranial magnetic stimulation therapy in which brain neurons are stimulated by the change in magnetic field.

BACKGROUND OF THE INVENTION

JP 5453325 B discloses a transcranial magnetic stimulation system. The system includes a head support and coil positioning unit for holding a head of patient in a proper position relative to a coil for transcranial magnetic stimulation during the transcranial magnetic stimulation treatment. WO2008/001003 discloses a device which robotically determines and moves the position of the components or devices, and a therapeutic apparatus that includes such device. In this apparatus, all moving parts in the transcranial magnetic stimulation device is robotized, and once the device memorizes the stimulation point in the patient's head, the transcranial magnetic stimulation coil assembly can automatically move to a position corresponding to the stimulation point.

The head support and coil positioning unit of JP 5453325 B, as its name implies, is to hold the patient's head and is not to detect that the head is not in the suitable position or to inform the patient of the fact. Therefore, the treatment can be continued as the coil is not in a position optimum for treatment. In this instance, an expected treatment effect may not be obtained. The system according to WO2008/001003 identifies the patient's head position using an infrared stereo camera, and then the robotic device automatically moves the transcranial magnetic stimulation coil assembly to a specified position to match the camera image with the MRI image. Unfortunately both the infrared stereo camera and the robotic device are considerably expensive, so that it is not economical to use such system for the general purpose therapies.

SUMMARY OF THE INVENTION

An object of the invention is to provide a transcranial magnetic stimulation system in which the patient may be easily arranged at the optimum position for treatment.

To this end, the transcranial magnetic stimulation system of the invention includes an optical device (502) for projecting a light spot (805) to a head of a patient and detecting a reflection light of the light spot (805);

a memory means (71) for memorizing information included in the reflection light detected by the optical device (502) as a reference information when the projected light spot (805) on the patient overlaps a marking (800) provided on the patient;

a calculation means (step #2) for calculating an overlap ratio between the marking (800) and the light spot (805) from the reference information memorized in the memory means (71) and a comparison information included in the reflection light of the light spot (805); and a display means (steps #5, #504) for displaying the overlap ratio.

In another aspect of the invention, each of the reference information and the comparison information includes a ratio of one or more light components included in the reflection light.

In another aspect of the invention, each of the reference information and the comparison information includes an intensity of the reflection light.

In another aspect of the invention, the system includes
a camera (503) configured to capture images of the light spot (805) projected on the patient and the marking (800); and
a display means (504) for displaying the images of the light spot (805) and the marking (800) captured by the camera (503).

In another aspect of the invention, the system includes a warning means (step #4, #802) for making a warning if the overlap ratio is below a predetermined value.

In another aspect of the invention, the system includes
a magnetic stimulation coil; and
a stopping means (#6, #802) for stopping a power supply to the magnetic stimulation coil if the overlap ratio is below a predetermined value.

In another aspect of the invention, the system includes
a head support mechanism configured to support the patient's head; and
a head detection mechanism configured to detect that patient's head is in contact with the head support mechanism.

In another aspect of the invention, the head support mechanism includes a headrest for supporting a back of the patient's head.

In another aspect of the invention, the system includes a warning means for making a warning when the head detection means detects that the head is out of contact with the headrest.

In another aspect of the invention, the system includes a chinrest (703) supporting a chin of the patient.

According to the transcranial magnetic stimulation system of the invention so constructed, the overlap ratio between the marking and the light spot is displayed, so that the it is easy to determine how the head is moved from the optimum position before and during treatment. The patient can move or return his or her head into the optimum position while viewing the overlap ratio. Also, in another aspect of the invention, the patient can readily recognize from the warning that his or her head is not in the optimum position. Further, in another aspect of the invention, the patient can readily recognize that his or her head is in or is not in the optimum position and then, if not, move or return his or her head into the optimum position before and during treatment.

PREFERRED EMBODIMENTS OF THE INVENTION

Referring to the accompanying drawings, a specific embodiment of the transcranial magnetic stimulation system (simply referred to as "the system", hereinafter) of the invention is described. It should be noted that the invention is not limited by the following descriptions relating to the exemplary embodiments.

1. General Construction

Figure 1:
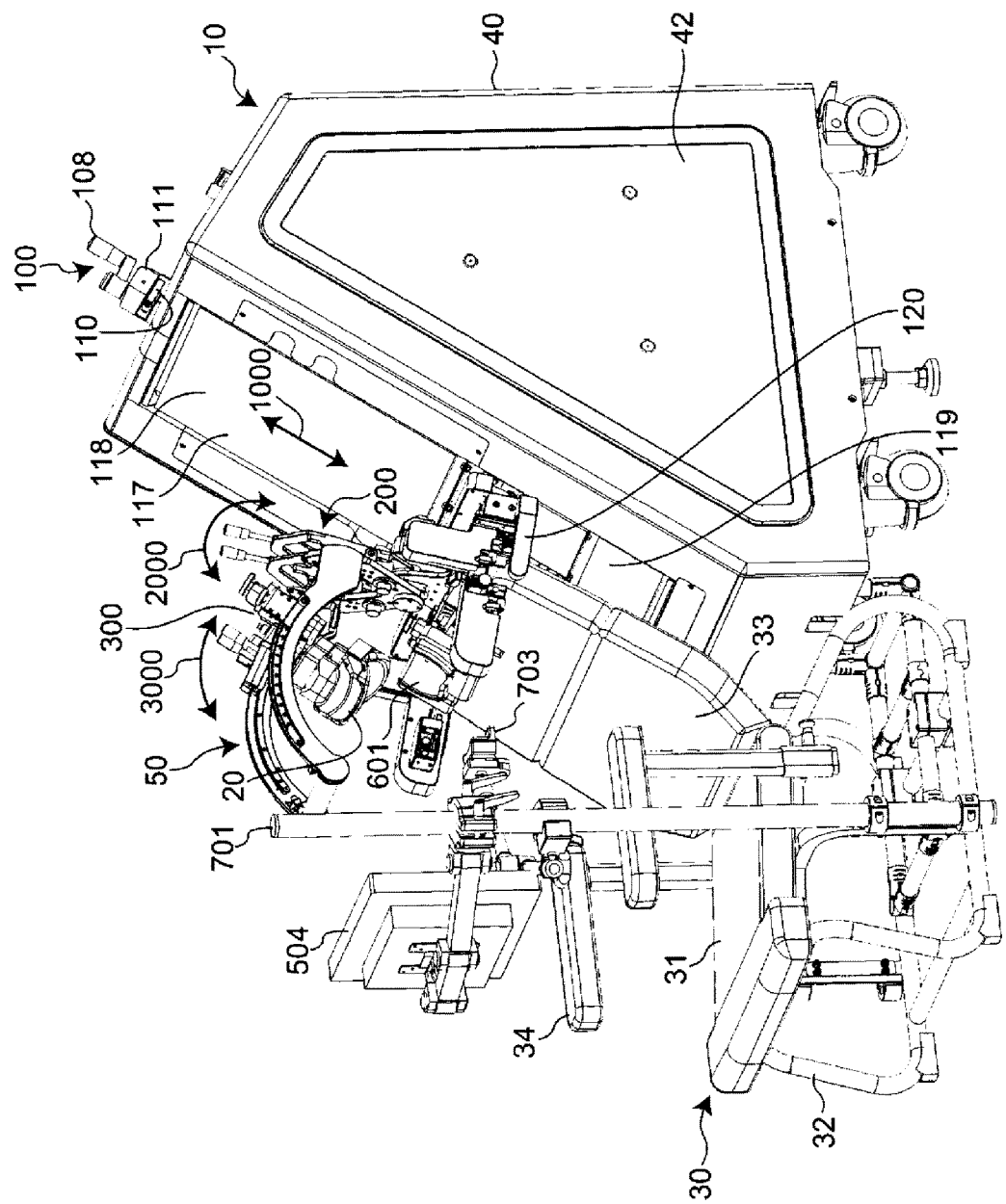
FIG. 1 is a perspective view of the transcranial magnetic stimulation system according to the invention.
Figure 2:
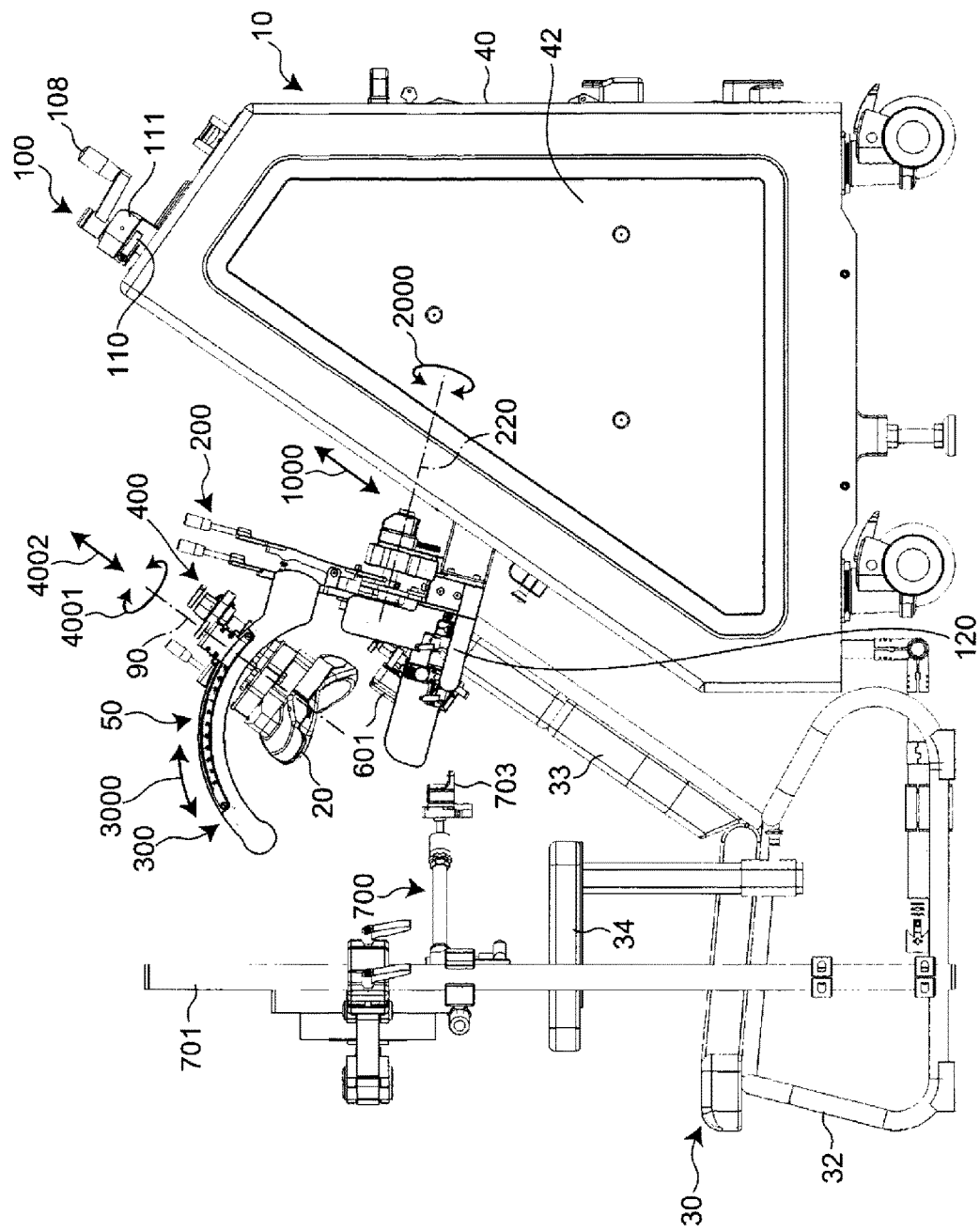
FIG. 2 is a side view of the transcranial magnetic stimulation system in FIG. 1.
Figure 3:
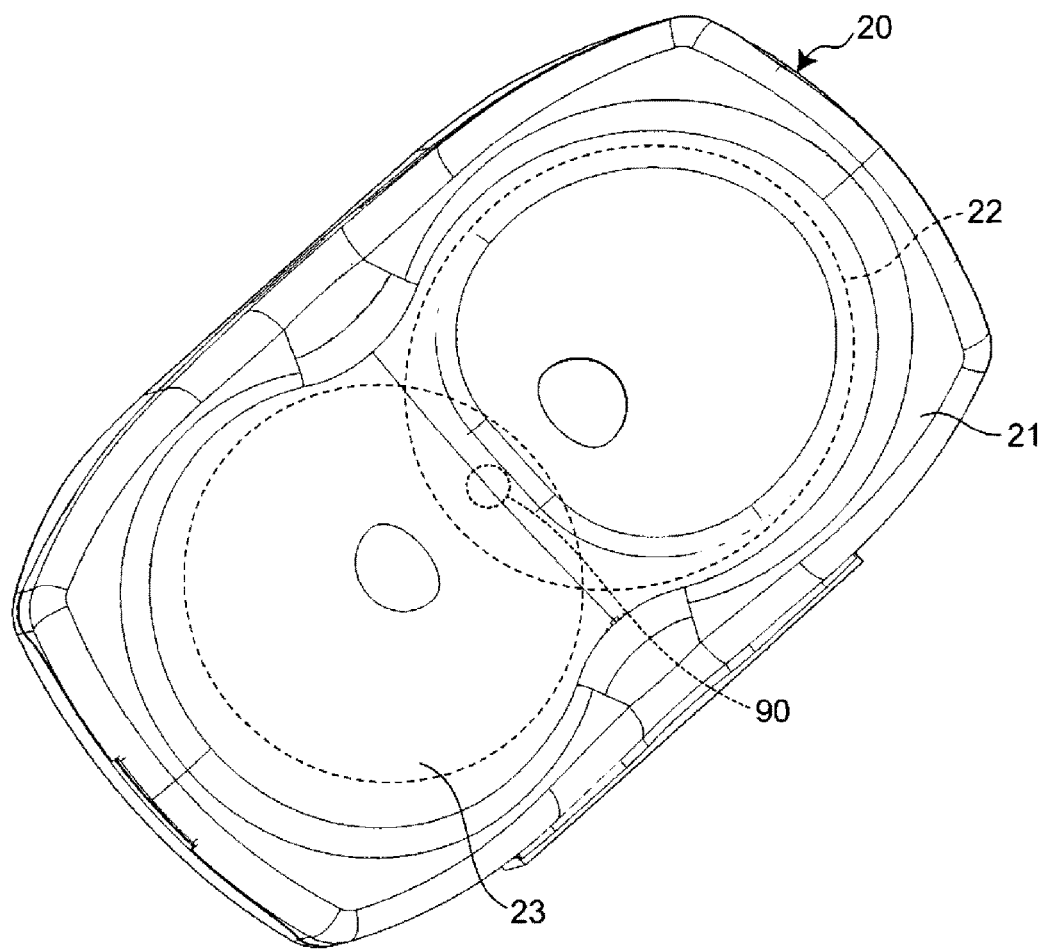
FIG. 3 is a perspective isolated view of the coil unit incorporated in the transcranial magnetic stimulation system in FIG. 1.

FIGS. 1 and 2 show a whole appearance of the system generally indicated by reference numeral 10. As illustrated, the system 10 includes a coil unit 20 for applying magnetic stimulation at a desired location in the patient's head. As shown in FIG. 3, in this embodiment, the coil unit 20 has a coil casing 21 which accommodates a figure-eight coil 22. Referring back to FIGS. 1 and 2, the system 10 also has a chair (support mechanism) 30 for supporting the patient during the treatment, and the adjustment mechanism and patient's head positioning mechanism (both described in detail below) for setting the coil unit at the proper position with respect to the patient sitting on the chair 30 in each treatment. Although, the chair is employed as the support mechanism in this embodiment, the support mechanism may be something like a bed, for example, as long as it is capable of stably supporting the patient at the treatment position.

2. Chair

In the embodiment, as shown in FIGS. 1 and 2, the chair 30 has a seat 31, legs 32, a back support 33, and left and right arm rests 34, similarly to regular chairs. Optionally, the arm rests may be eliminated. In the embodiment, the back support 33 is inclined at a predetermined angle (e.g., approximately 35 degrees from the vertical plane, and approximately 55 degrees from the horizontal plane), so that the patient may be seated in a relaxed posture. For the purpose of the spatial description of components hereinafter, with respect to the patient sitting on the chair 30, the left hand side and the right hand side of the patient is referred to as the left hand side and the right hand side of the system 10, respectively. Also, one side adjacent the patient sitting on the chair 30 is referred to as "front portion" or "front side", and the other side backwardly away from the patient sitting on the chair 30 is referred to as "rear portion" or "rear side".

3. Housing

As shown in FIGS. 1, 2, 4, and 5, the housing 40 of the system 10 includes a frame 41 (see FIG. 5) forming a whole structure of the system and a plurality of panels 42 (see FIGS. 1, 2, 4) covering the frame 41. Although not shown, a power source 80 (see FIG. 23) for supplying power to the coil and a controller 70 (see FIG. 23) for driving the power source 80 to control electric current applied to the coil 22 are accommodated within a space surrounded by the panels 42. In the embodiment, as shown in the drawing, the front frame portion 43 (see FIG. 5) is tilted backward according to the inclination of the back support 33 of the chair 30.

4. Adjustment Mechanism

Adjustment mechanism has an elevating mechanism (fifth mechanism) 100, a rolling mechanism (first mechanism) 200, a pitching mechanism (second mechanism) 300, yawing/moving mechanisms (third and fourth mechanisms) 400, for example, in order to adjust, respectively, a height, a position in the left and right direction, a position in the back and forth direction, an angle around the coil center axis (yawing axis) 90 (see FIG. 13) of the coil unit 20, and a distance between the patient's head and the coil, with respect to the patient sitting on the chair 30.

The elevating mechanism 100 (fifth mechanism) is provided for adjusting the height of the coil unit 20 with respect to the patient by moving the coil unit 20 up and down. As shown in FIGS. 1 and 2, the elevating mechanism 100 adjusts the height of the coil unit by moving the coil unit in an inclined direction substantially similar to the tilting direction of the back support 33 (i.e., direction illustrated by an arrow 1000 in FIGS. 1 and 2).

The rolling mechanism 200 (first mechanism) is provided for rolling the coil unit 20 in the left and right direction (i.e., direction illustrated by an arrow 2000) around an axis (rolling axis) 220 extending obliquely and upwardly from the rear side to the front side as shown in FIG. 2, so that the coil unit 20 pivotally moves in the left and right direction along the surface of the patient's head.

The pitching mechanism 300 (second mechanism) is provided for pitching the coil unit 20 in the back and forth direction (i.e., direction illustrated by an arrow 3000) around an axis (pitching axis) 320 (see FIG. 11) extending in the left and right direction orthogonal to the rolling axis 220 as shown in FIGS. 1 and 2, so that the coil unit 20 pivotally moves in the back and forth direction along the surface of the patient's head.

The yawing/moving mechanism 400 (third mechanism and fourth mechanism) is provided for yawing the coil unit 20 in the direction illustrated by an arrow 4001 around the yawing axis 90 extending orthogonal to the pitching axis 320 as shown in FIG. 2 to adjust the orientation (yawing angle) of the coil unit 20 with respect to the patient's head and for moving the coil unit 20 to and from the patient's head in the direction illustrated by an arrow 4002 along the yawing axis 90 to adjust the distance between the coil unit 20 and the patient's head.

Preferably, each of the first through fifth mechanisms includes a mechanism for braking the movement of the coil unit, and a mechanism for locking the position of the coil unit. The braking mechanism allows an easy adjustment of the coil position. The locking mechanism securely holds the position of the coil during the treatment. More preferably, each of the first through fifth mechanisms includes a position indicating mechanism showing the position of the coil unit. The position indicating mechanism allows users to see the position of the coil unit and to readily reproduce the position of the coil unit.

In the embodiment, the mounting unit 50 is connected to the elevating mechanism 100 (see FIGS. 1, 2, 4, and 6). The rolling mechanism 200 is supported by the mounting unit 50. The pitching mechanism 300 is supported by the rolling mechanism 200. The yawing/moving mechanism 400 is supported by the pitching mechanism 300. Each of those mechanisms will be described hereinafter.

4-1. Elevating Mechanism 100 (Fifth Mechanism)

Figure 5:
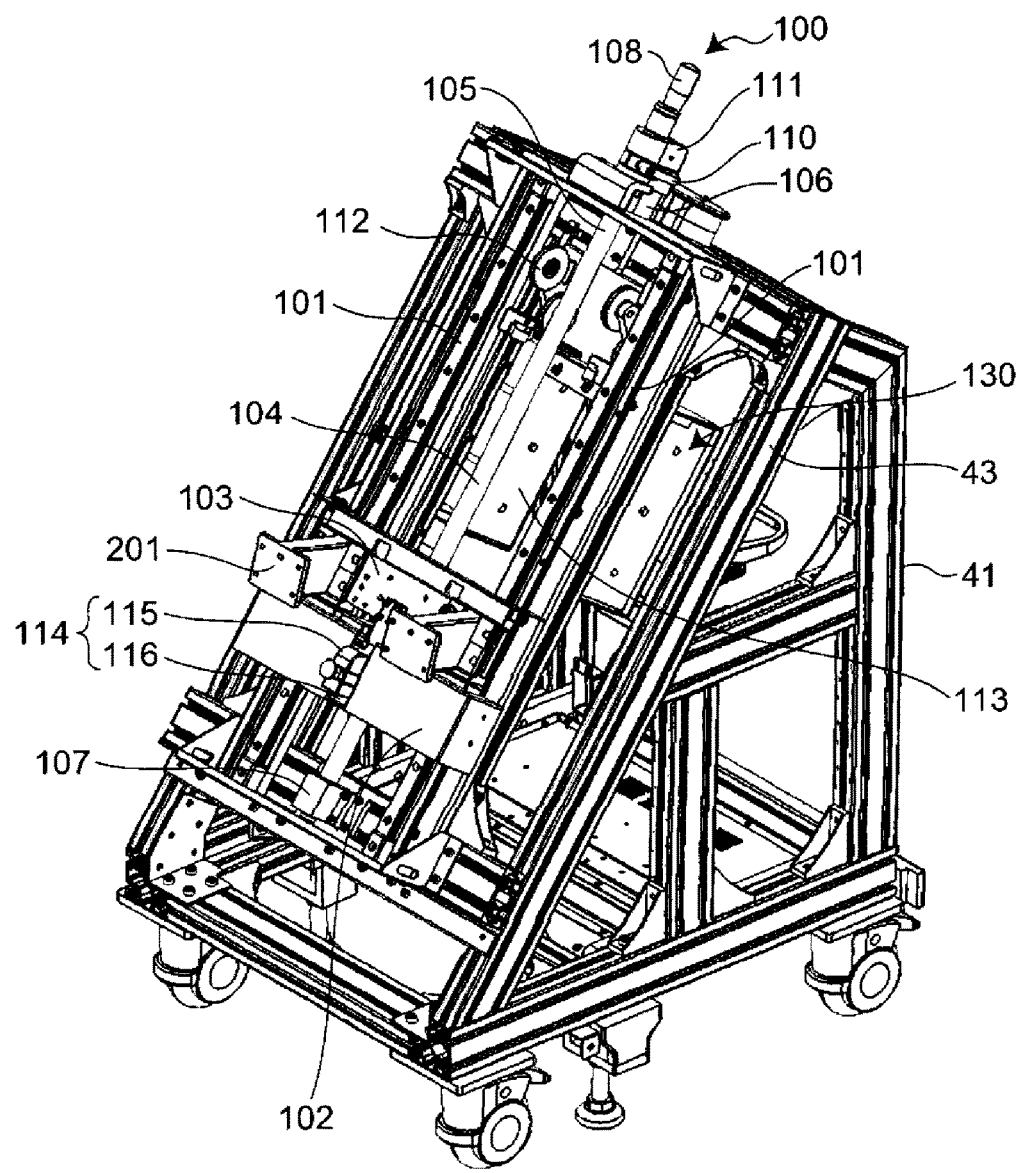
FIG. 5 is a perspective view of the housing and the elevating mechanism of the transcranial magnetic stimulation system in FIG. 1+
Figure 6:
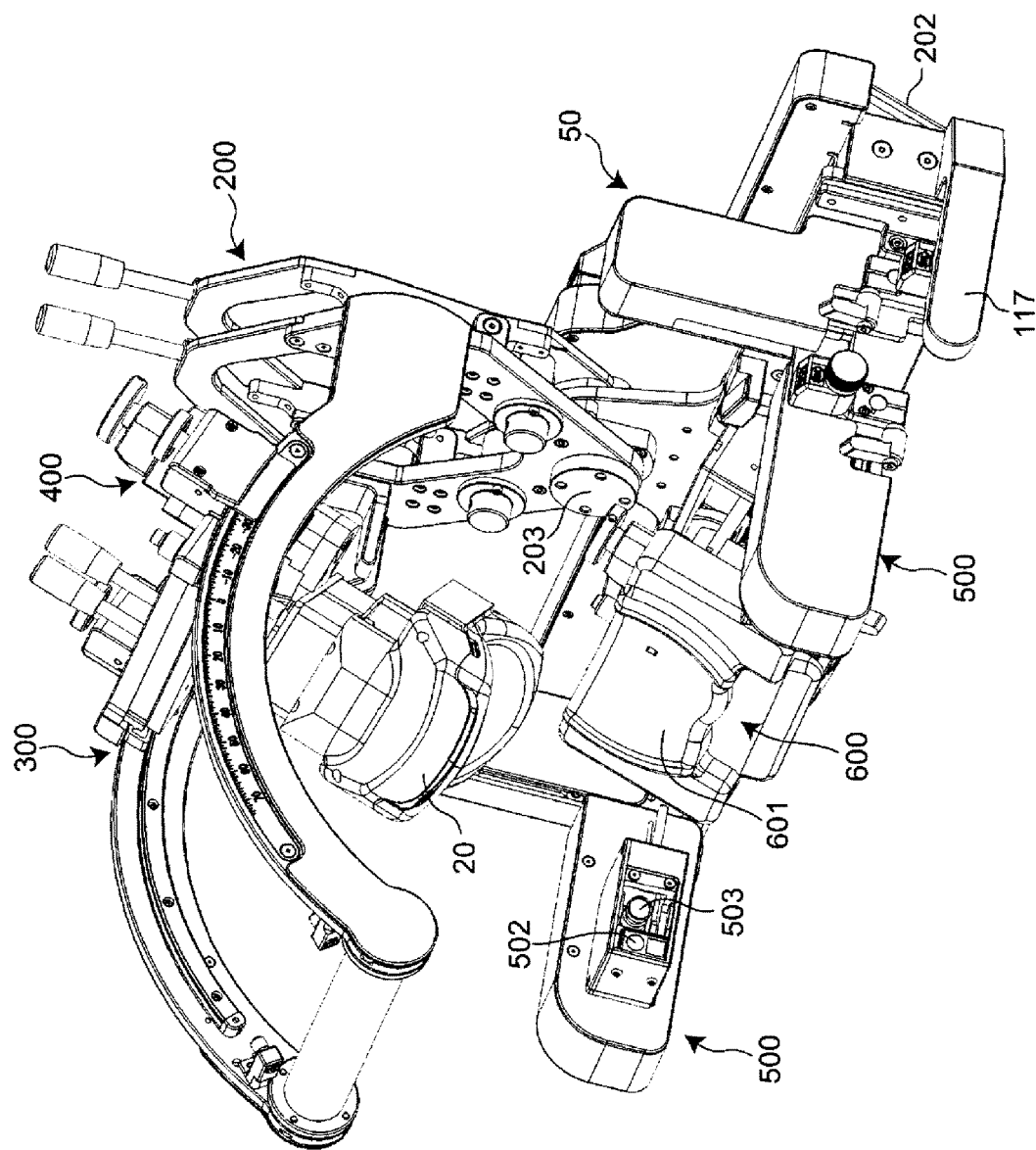
FIG. 6 is a perspective view showing the mounting unit of the transcranial magnetic stimulation system in FIG. 1.

Referring to FIG. 5, the elevating mechanism 100 includes guides or guide rails 101 securely mounted on the front frame portion 43 of the system housing 40. The guide rails 101 are oriented in a direction parallel to or substantially parallel to the median line of the patient sitting in the chair 30. In the embodiment, the paired guide rails 101 are securely mounted substantially in parallel to each other as they are spaced a distance away from each other in the left and right direction, with an inclination corresponding to the inclination of the front frame portion 43. The guide rails 101 support two carriages, including lower carriage 102 (first carriage) and upper carriage 103 (second carriage), capable of moving up and down along the guide rails 101.

The lower carriage 102 is connected to a transporting mechanism 104 which transports the lower carriage 102 up and down according to the manual operation by an operator. For example, the transporting mechanism 104 includes a threaded shaft 105 (external threaded member) positioned between and parallel to the guide rails 101, shaft bearings 106, 107 rotatably supporting unthreaded portions defined in the top and bottom ends of the threaded shaft 105, and a handle 108 securely connected to the top end of the threaded shaft 105. A nut (not shown), which is fixed to the lower carriage 102, holds the threaded shaft 105 threadedly inserted in the nut. This allows that, by the rotation of the threaded shaft 105 with the handle 108, the lower carriage 102 moves up or down along the guide rails 101. Preferably, a locking mechanism 110 is provided, for example, adjacent the handle 108, to prevent the unwanted free rotation of the threaded shaft 105.

Preferably, a mechanism which indicates the position or the height of the lower carriage 102 is provided. In the embodiment, an indicator 111 is provided adjacent the handle 108, allowing users to see or reset the height of the coil unit 20.

The upper carriage 103 supports the mounting unit 50 (see FIGS. 1, 2, 4, and 6). Preferably, the elevating mechanism includes a sub-mechanism for reducing load caused in elevating the coil mounting unit. In the embodiment, as shown in FIG. 5, the upper carriage 103 is connected to a spring mechanism 130 for reducing the load which causes during the elevation of the upper carriage 103. The spring mechanism 130 includes a wire (not shown) connected at one end thereof to the upper carriage 103. The wire is connected to a constant force spring 113 through one or more pulleys arranged behind the upper portion of the guide rail 101. The constant force spring 113 is selected so that the operator may elevate the mounting unit 50 connected to the upper carriage 103 smoothly with a constant small force. This allows the upper carriage 103, together with the mounting unit 50, to be elevated with a light force.

In the embodiment, the lower and upper carriages 102 and 103 has a locking mechanism 114 which detachably locks the upper carriage 103 against the lower carriage 102 when the upper carriage 103 takes a position most adjacent the lower carriage 102. For example, the locking mechanism 114 may be made of a spring-biased engagement portion (e.g., a hook) 115 provided in one carriage and a mating engagement portion 116 provided in the other carriage.

The locking mechanism 114 is to prohibit the relative movement between the lower carriage 102 and the upper carriage 103, not to prohibit them from elevating together. This means that, the lower carriage 102 together with the upper carriage 103 locked against the lower carriage 102 can be elevated by rotating the threaded shaft 105 with handle 107.

In the embodiment, a handle 120 (see FIGS. 1, 2, and 4) provided for an operator to elevate the upper carriage 103 and the coil mounting unit 50 supported by the upper carriage 103. Therefore, the operator, with his or her hand holding the handle 120, can unlock the locking mechanism 114 and thereby separate the upper carriage 103 from the lower carriage 102, as necessary. This in turn allows that, when any trouble occurs during the treatment or in case of emergency (e.g., when the patient feels discomfort during the treatment), the operator can lift the mounting unit 50 and the coil unit 20 supported by the mounting unit 50 up away from the patient as quickly as possible.

Figure 4:
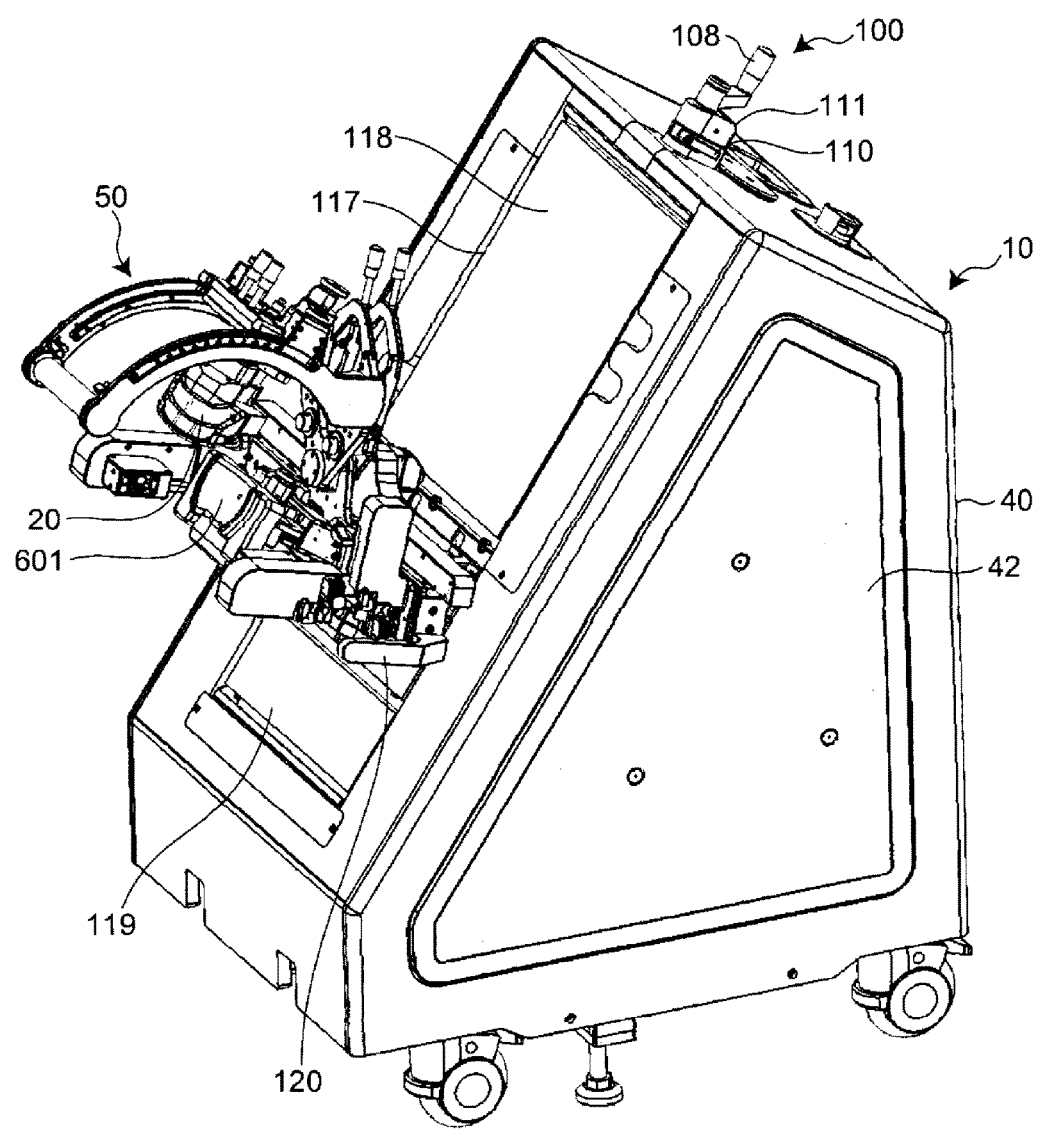
FIG. 4 is a partial perspective view of the transcranial magnetic stimulation system in FIG. 1.

In the embodiment, as shown in FIG. 4, the front portion of the system housing 40 has an opening 117 defined in a region where the lower and upper carriages 102 and 103 elevate. As shown, the opening 117 is closed by shutters 118 and 119 or bellows curtains which expand and contract with the movements of the lower and upper carriages 102 and 103.

4-2. Rolling Mechanism 200 (First Mechanism)

Figure 7:
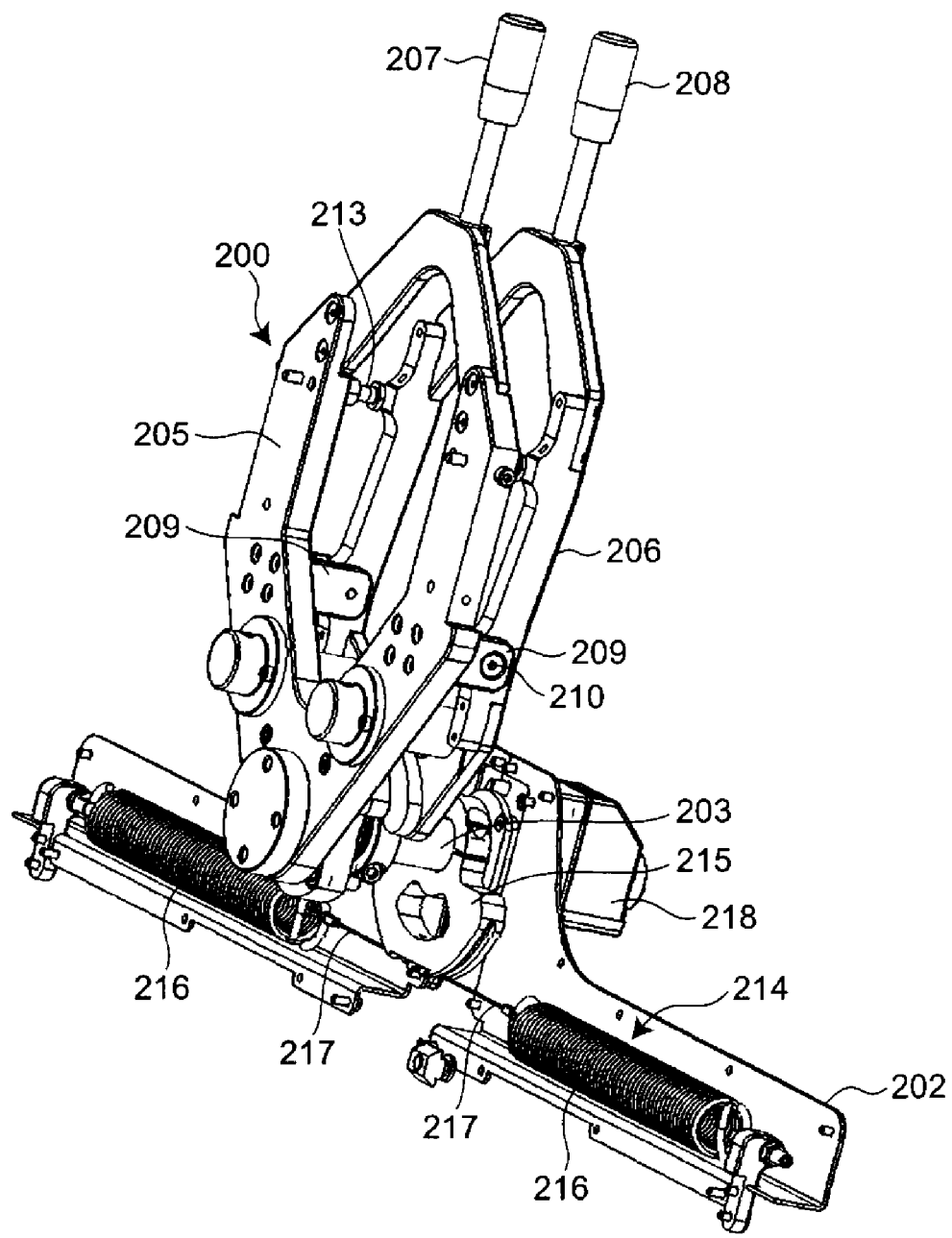
FIG. 7 is a perspective view showing the rolling mechanism of the transcranial magnetic stimulation system in FIG. 1.
Figure 8:
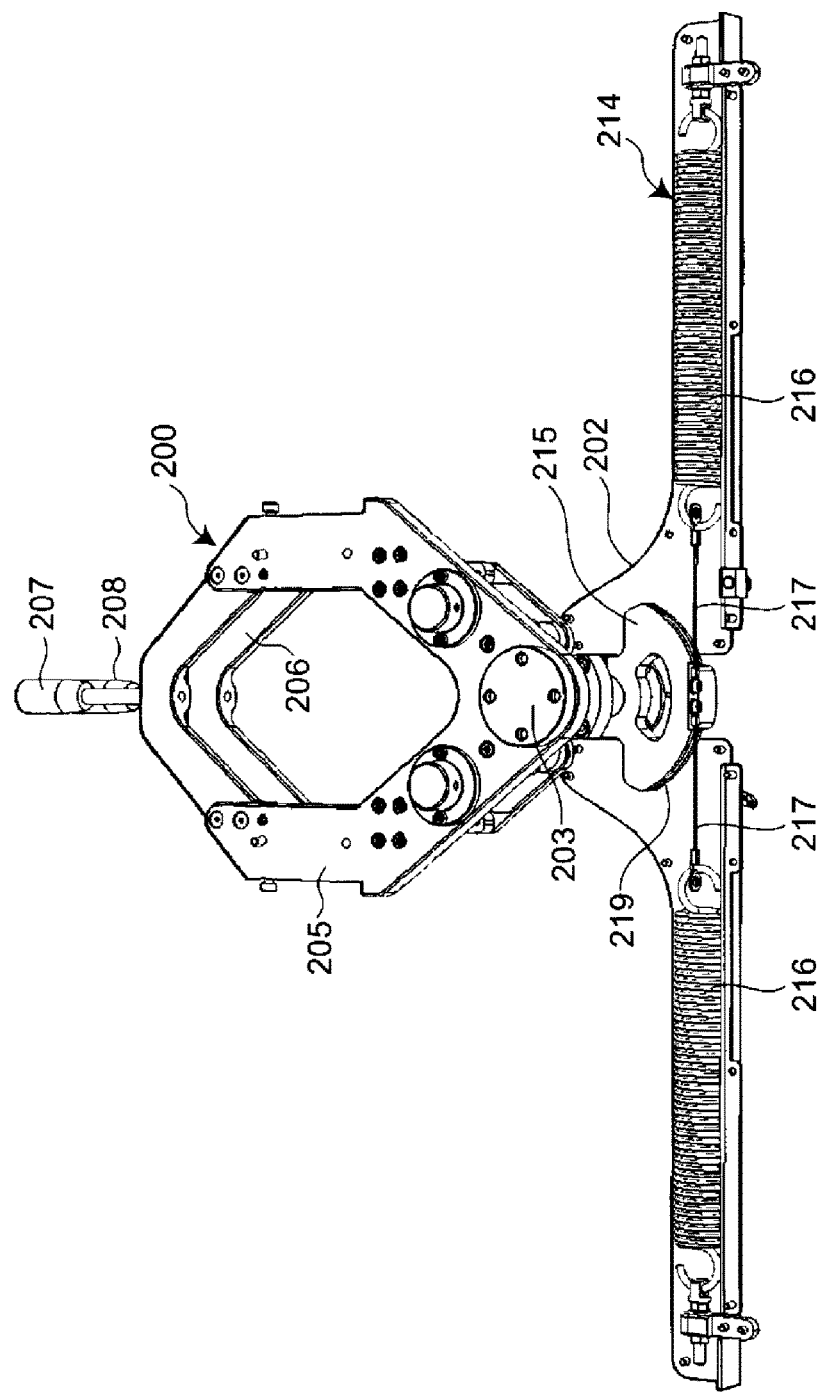
FIG. 8 is a perspective view showing the rolling mechanism of the transcranial magnetic stimulation system in FIG. 1.
Figure 9:
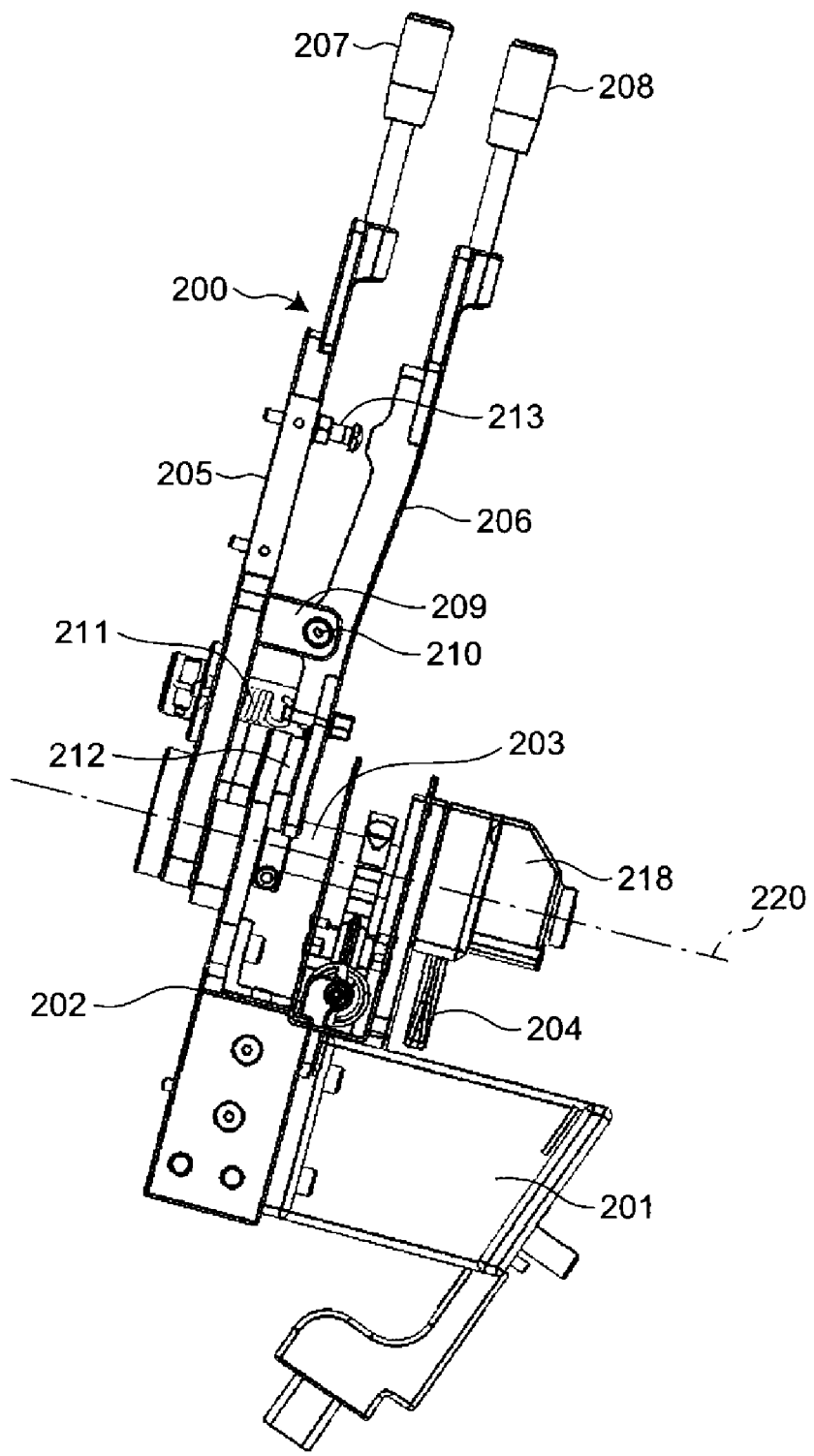
FIG. 9 is a side view showing the rolling mechanism of the transcranial magnetic stimulation system in FIG. 1.

As shown in FIGS. 6-9, the rolling mechanism 200 includes a frame 202 which is fixed on the upper carriage 103 through a bracket 201 (see FIG. 9). The fixed frame 202 supports a rolling shaft 203 extending along a rolling axis (first axis) 220 (see FIG. 9), for rotation around the rolling axis 220. This allows that the rotation of the rolling shaft 203 cause the coil 22 supported through, for example, a roll plate described below to pivot in the left and right direction along an imaginary curved surface (first imaginary surface) around the rolling axis 220. The imaginary surface may be circular or elliptic. As illustrated, the rolling shaft 203 is oriented obliquely and upwardly from the rear to the front direction. An angle defined between the vertical axis (not shown) and the rolling shaft 203, which is determined so that the coil 22 mounted in the coil mounting unit 50 can scan a predetermined region of the patient's head, is approximately 75 degrees, for example. In the embodiment, the fixed frame 202 includes a locking mechanism 204 (see FIG. 9) which locks the rolling shaft 203 against the fixed frame 202 and thereby prevents an unwanted rotation of the rolling shaft 203 to the fixed frame 202.

The rolling shaft 203 securely supports a front roll plate 205. In the embodiment, the front roll plate 205 is made of a substantially hexagonal frame. A rear roll plate 206, which is also substantially hexagonal and substantially similar to the front roll plate 205, is placed behind the front roll plate 205. A front handle 207 and a rear handle 208 are attached on the top ends of the front roll plate 205 and the rear roll plate 206, respectively.

The rear roll plate 206 is supported for rotation by a pair of brackets 209 extending rearward from the left and right central portions of the front roll plate 205 through connection shaft 210 extending in the transverse direction orthogonal to the rolling shaft 203, which allows that front and rear roll plates 205 and 206 to rotate with the rolling shaft 203.

In order to brake or prevent rolling of the front roll plate and the coil unit supported on the front roll plate 205 relative to the rolling shaft 203 in a period of time during which the rolling angle is fixed and not being adjusted, the front and rear roll plates 205 and 206 are connected by the left and right tension coil springs 211 (see FIG. 9) provided in a region below the connection shaft 210 to pull the front and rear roll plates 205 and 206 close to each other and also a friction plate 212 or member is provided between the lower portions of the rear roll plate 206 and the fixed frame 202. In a normal condition in which the rolling angle is fixed, the friction plate 212 is sandwiched between the rear roll plate 206 and the fixed frame 202 due to the biasing force from the tension coil springs 211.

This prevents the unwanted rotation of the rear roll plate 206 and the front roll plate 205 connected to the rear roll plate 206 relative to the fixed frame 202. When adjusting the rolling angle, the operator grasps the front and rear handles 207 and 208 of the front and rear roll plates 205 and 206 to bring them closer together by his or her one hand and thereby separate the rear roll plate 206 or the fixed frame 202 from the friction plate 21, which allows the front and rear roll plates 205 and 26 to rotate with the rolling shaft 203. The friction plate 212 may optionally be fixed to the fixed frame 202 or the rear roll plate 206.

As described above, the rotation of the front and rear roll plates 205 and 206 is initiated simply by eliminating the engagement between the rear roll plate 206 or the fixed frame 202 and the friction plate 212, which only requires a slight movement of the rear roll plate 206 toward the front roll plate 205. For this purpose, in the embodiment, a projection 213 projecting toward the rear roll plate 206 is provide at an upper portion of the front roll plate, above the connection shaft 210, to prevent a further rotation or movement of the rear roll plate 206 beyond a position where the projection 213 is in contact with the rear roll plate 206.

In the embodiment, as shown in FIGS. 7 and 8, a spring mechanism (load reduction mechanism) 214 is provided to reduce the load acting on the handles 207, 208 during the left or right pivotal rolling movement of the coil unit 20. The load reduction mechanism is not limited to the spring mechanism as long as the load which causes during the left or right pivotal rolling movement of the coil unit is reduced. The load reduction mechanism allows users to move the coil unit easily and precisely. The spring mechanism 214 includes a rotation plate 215 fixed to the rolling shaft 203, and coil springs 216 mounted on the fixed frame 202 on the opposite left and right sides of the rotation plate 215.

One end of each coil spring 216 (the distal end away from the rotation plate 215) is connected to the fixed frame 202 and the other end is connected to the circumference of the rotation plate 215 through a string or a wire 217. Thus, when the rolling shaft 203 rotates clockwise in FIG. 8 relative to the fixed frame 202, the wire 217 at the right hand side is pulled as it is wound up around the circumference of the rotation plate 215 and the coil spring 216 at the right hand side in FIG. 8 is extended to generate a force urging the rolling shaft 203 rearward (counterclockwise). When the rolling shaft 203 rotates counterclockwise in FIG. 8 relative to the fixed frame 202, the spring at the left hand side in FIG. 8 is extended to generate a force urging the rolling shaft 203 to the other direction.

As described above, when the operator holds the handles 207 and 208 and moves the coil unit 20 to the left or right in the rolling motion, a force resisting the force applied to the handles is generated by the coil springs to reduce the load acting on the handles 207, 208. In order to ensure that the wire 217 winds around the periphery of the rotation plate 215 with the rotation of the rolling shaft 203, preferably a groove 219 is provided on the periphery of the rotation plate 215 to receive the wire 217 in the groove.

Preferably, a mechanism for indicating an angle of rotation of the rolling shaft 203 (rolling angle) is provided. In the embodiment, an indicator 218 is provided behind the rear roll plate 206 to confirm or set the rolling angle of the coil unit 20.

4-3. Pitching Mechanism 300 (Second Mechanism)

Figure 10:
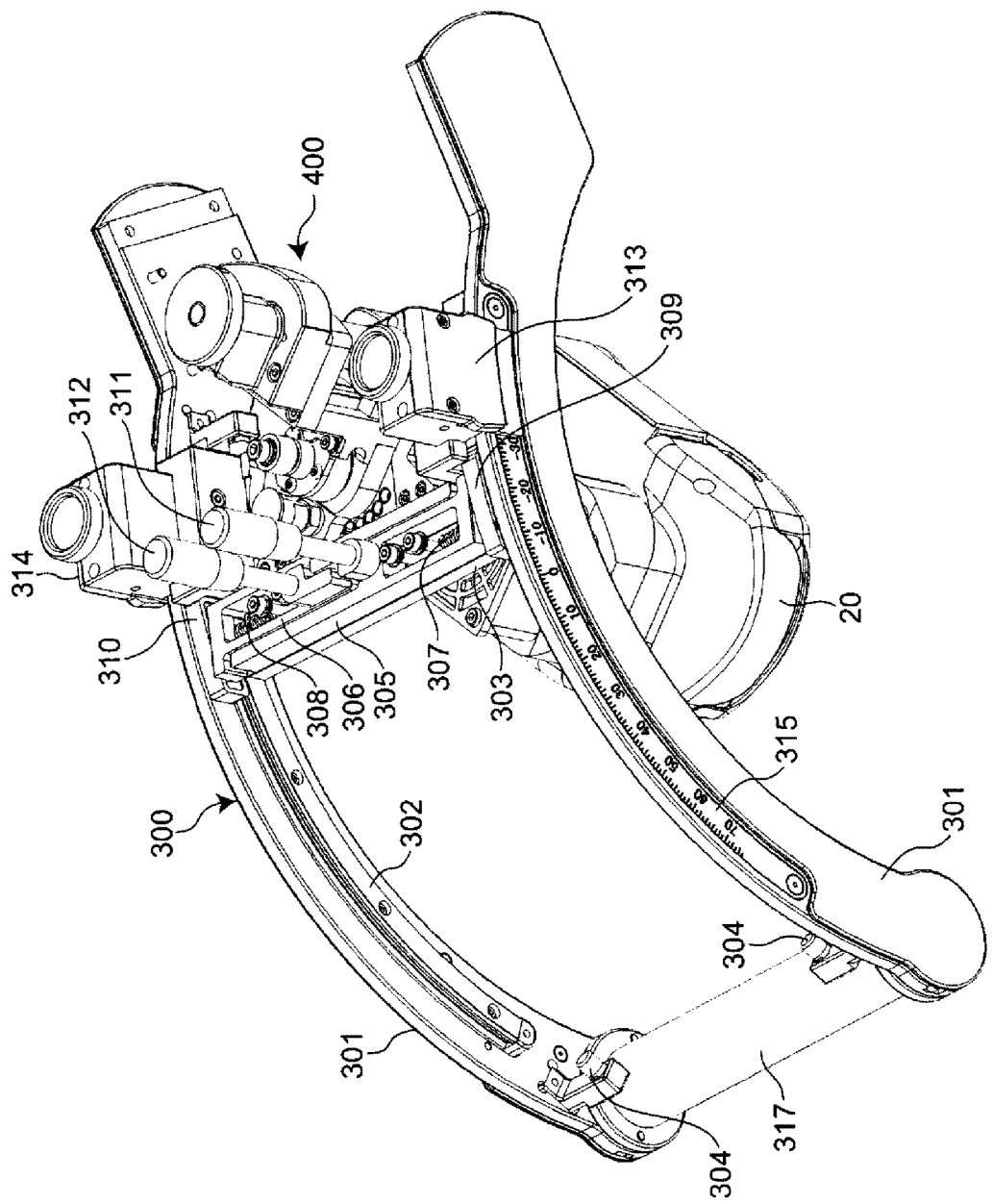
FIG. 10 is a perspective view showing the pitching mechanism of the transcranial magnetic stimulation system in FIG. 1.
Figure 11:
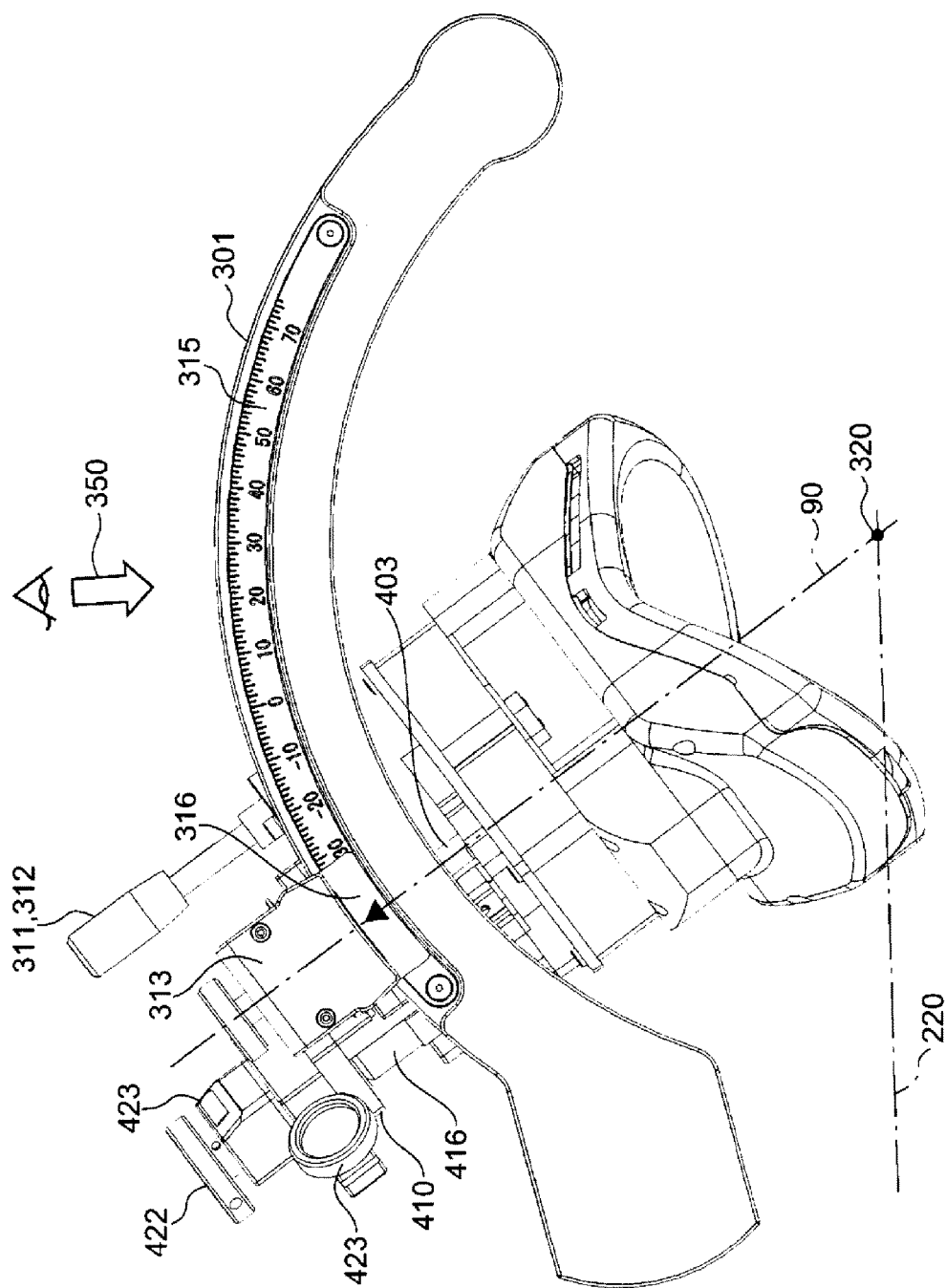
FIG. 11 is a side view showing the pitching mechanism of the transcranial magnetic stimulation system in FIG. 1.
Figure 12:
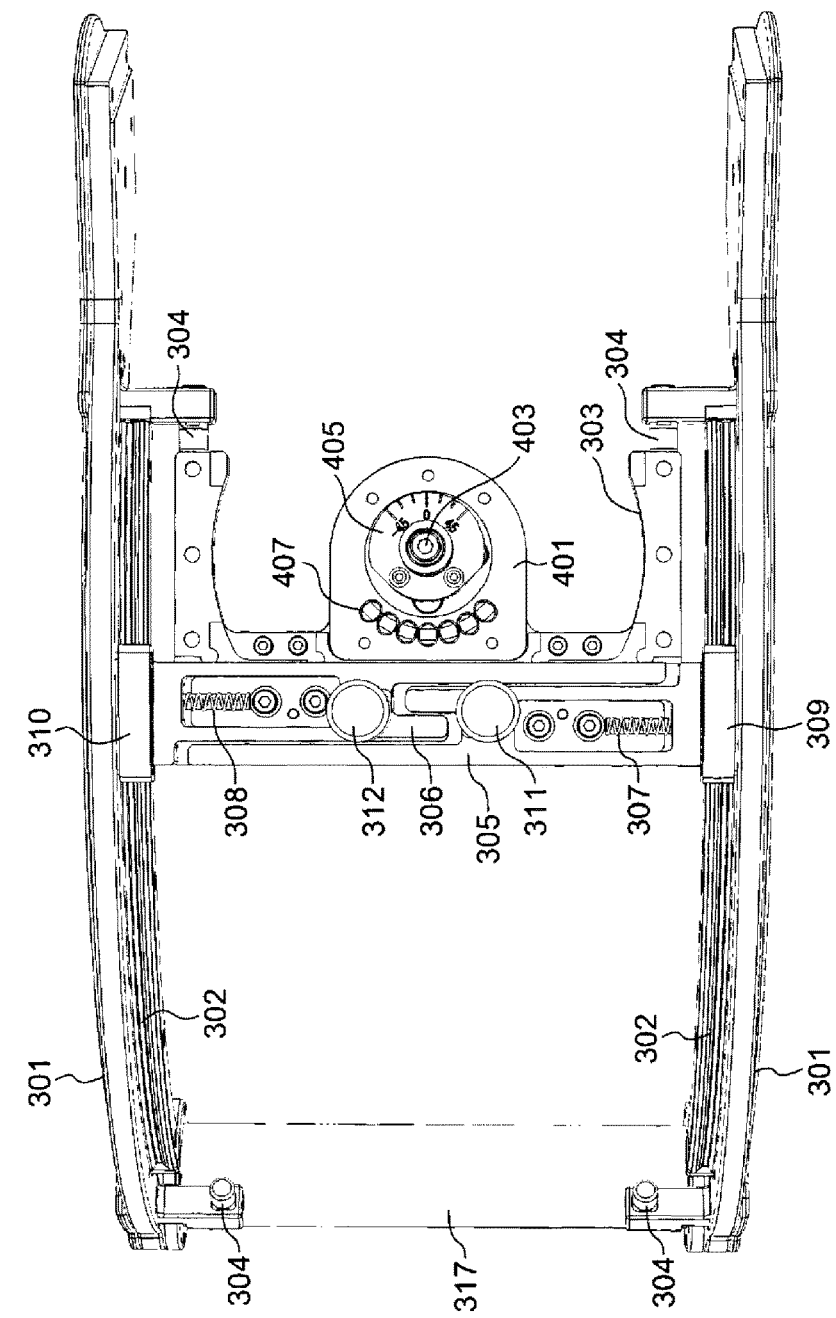
FIG. 12 is a perspective view showing the pitching mechanism of the transcranial magnetic stimulation system in FIG. 1.

As shown in FIGS. 10, 11, and 12, the pitching mechanism 300 includes a pair of arc-shape arms 301 extending in parallel to each other and forward from the left and right ends of the front roll plate 205. As illustrated in FIG. 11, the arms 301 project forward along respective arches extending about the pitching axis (second axis) 320 below the arm 301. In the embodiment, the pitching axis 320 extends orthogonal to the rolling axis (first axis) 220 of the rolling shaft 203. The term "orthogonal" means that the pitching axis 320 is orthogonal or substantially orthogonal to the rolling axis 220 when viewed in a radial direction (indicated by arrow 350) from the rolling axis 220. This in turn means that the invention includes not only embodiments in which the rolling axis 220 and the pitching axis 320 intersect with each other as indicated in FIG. 11 but also embodiments in which the rolling axis 220 and the pitching axis 320 do not intersect with each other and are spaced away from each other in the direction indicated by arrow 350.

Each of the arms 301 includes a guide rail 302 which extends along the arm in the arc-shape about the pitching axis 320. In the embodiment, the guide rail is provided on an inner surface of the arm opposing the inner surface of the other arm. Preferably, the guide rail 302 includes a mechanism which reduces the load to be caused in the back and forth pivotal pitching movement of the coil. For example, a ball circulation type guide rail is used for the guide rail. The guide rails 302 supports a pitching frame (pitching plate) 303 (see FIG. 12) so that the pitching frame can pivotally move along the guide rail 302 in the back and forth direction. Each of the guide rails 302 has stops 304 provided at the front and rear portions of the guide rail 302 in order to delimit the range of the back and forth movement of the pitching frame 303. The distal ends of the arms 301 are connected to each other by a connection member 317.

The pitching frame 303 includes a pair of brake plates 305 and 306 which are supported to move in the left and right direction along the top surface of the pitching frame 303. The left and right brake plates 305, 306 are forced to the left and to the right respectively (i.e., outwardly) by corresponding coil springs 307 and 308, so that the brake pads 309 and 310 attached to the outside end surfaces of the left and right brake plates 305, 306 are forced against the inside surface of the corresponding left and right arms 301, which results in that the pitching frame 303 is fixed to the arms 301 immovably in the back and forth direction. As illustrated, brake releasing handles 311 and 312 are mounted to the left and right brake plates 305 and 306, respectively, so that, when the operator grasps the left and right brake releasing handles 311, 312 together to bring them closer together by his or her one hand to break a contact between the left and right brake pads 309 and 310 and the arms 301, the pitching frame 303 and the coil unit 20 can move in a pitching motion in the back and forth direction. In order to lock the pitching frame 303 against the arm 301, locking mechanisms 313 and 314 (see FIG. 10) are provided at the left and right portions of the pitching frame 303, corresponding to left and right arms 301.

Preferably, a mechanism is provided to indicate the position of the coil unit 20 in the back and forth direction. In this embodiment, a scale 315 (a part of the indicator) is provided on the outside surface of the arm 301, and a scale index plate 316 (a part of the indicator) is provided on the locking mechanism 313, 314 of the pitching frame 303, which allows that, by reading the scale 315 value pointed by the scale index plate 316, the position of the coil unit 20 in the back and forth direction, or pitching angle, can be confirmed. Therefore, in the embodiment, by using the indicator with the scale 315 and the scale index plate 316, the pitching angle of the coil unit 20 can be confirmed or can be set, by reading the scale 315 value pointed by the scale index plate 316.

When moving in the back and forth direction along the arm 301, the coil pivotally moves on the imaginary curved surface (second imaginary curved surface) around the pitching axis 320. Although the trajectory of the coil casing 21 pitching about the pitching axis 320, i.e., the coil casing surface 23 opposing the patient's head (in particular, head contact surface) of the coil casing 21 may draw a circle or ellipse, the curvature of the imaginary curved surface is preferably determined to be similar to that of average adult's head surface portion passing his or her median line. Preferably, the height of the arm 301 from the rolling axis 220 is determines so that the curvature of the trajectory of the casing surface 23 rolling in the left and right direction about the rolling axis 220 is similar to that of average adult's head surface (in particular, front head surface).

4-4. Yawing/Back-and-Forth Mechanism 400 (Third Mechanism and Fourth Mechanism)

Figure 13:
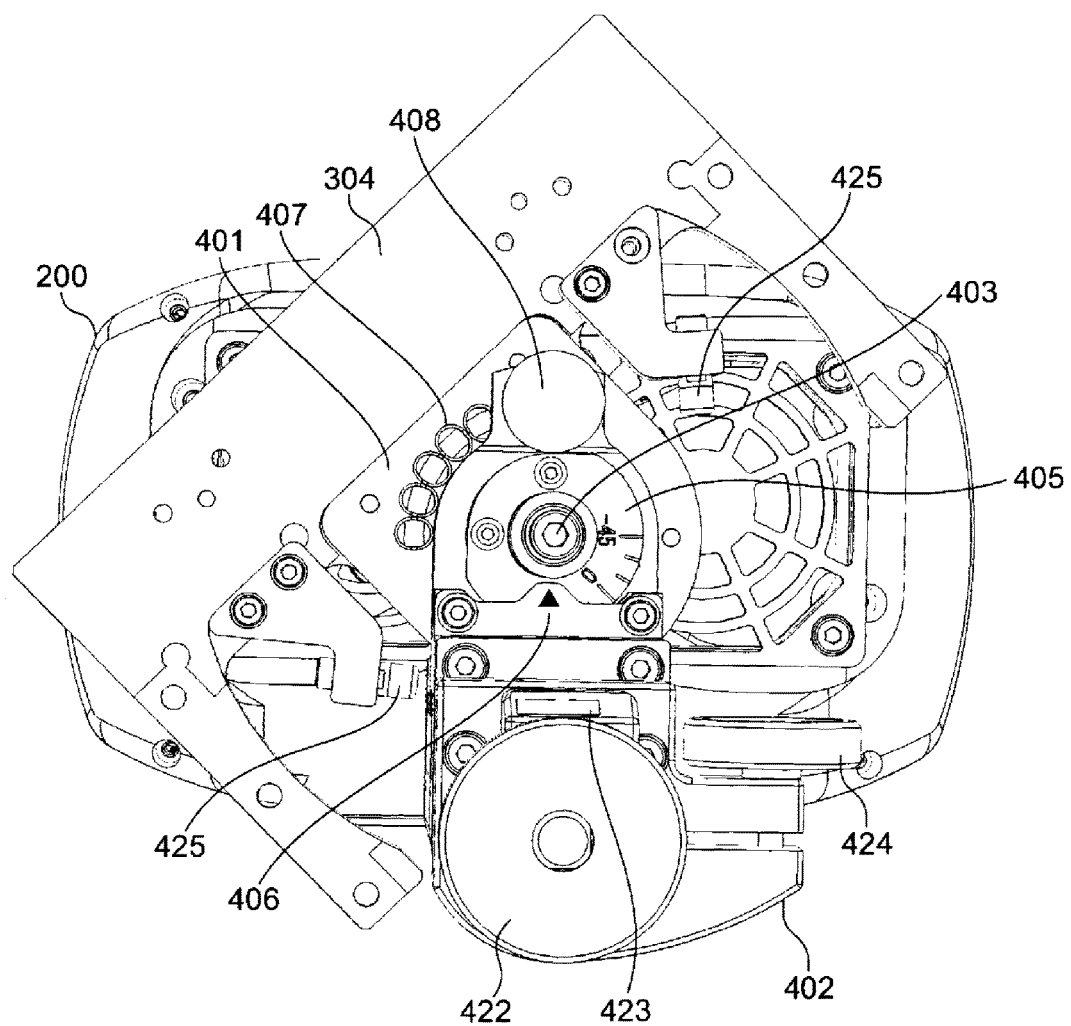
FIG. 13 is a perspective view showing the yawing/moving mechanism of the transcranial magnetic stimulation system in FIG. 1.
Figure 14:
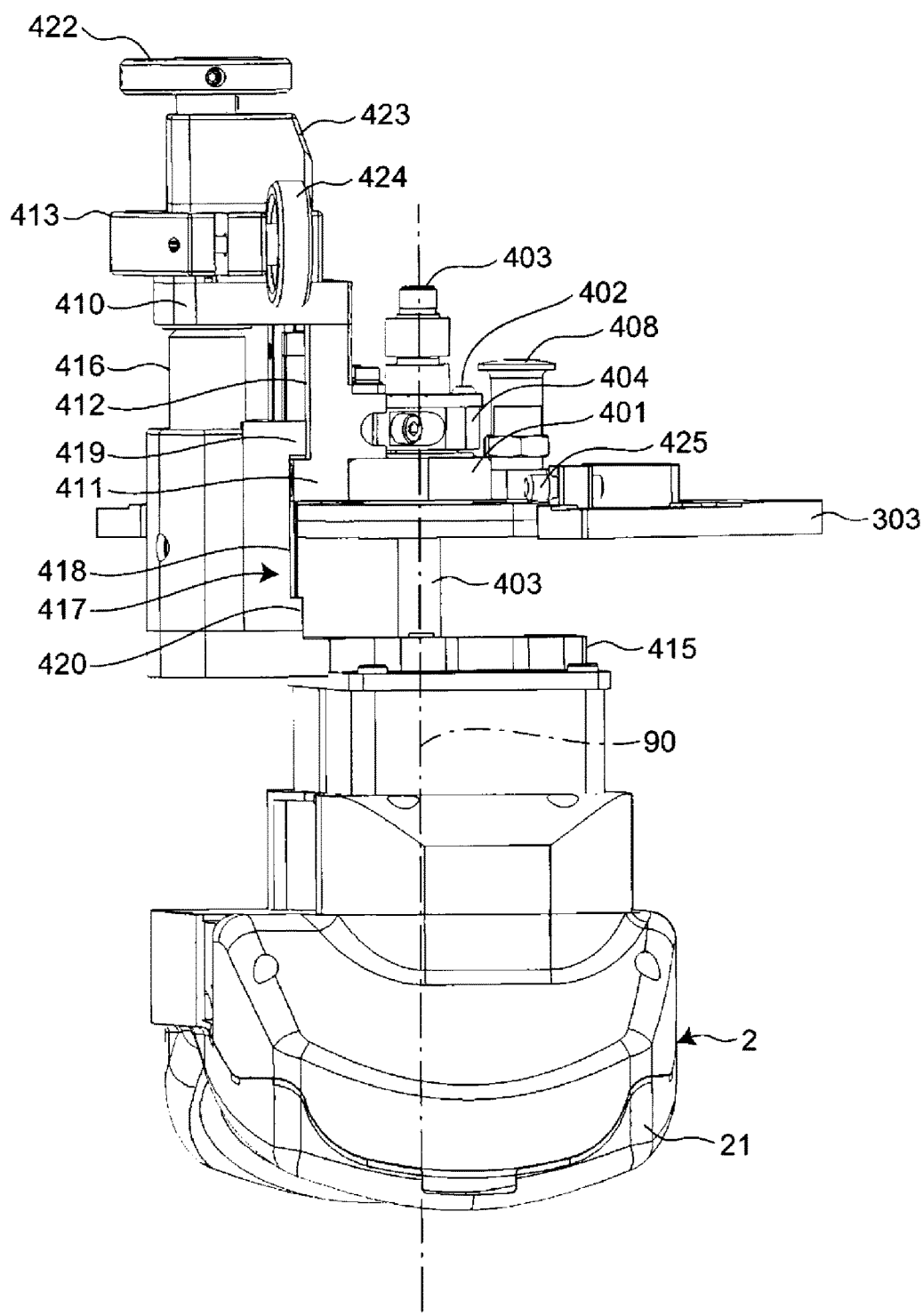
FIG. 14 is a perspective view showing the yawing/moving mechanism of the transcranial magnetic stimulation system in FIG. 1.

As illustrated in FIGS. 13 and 14, the yawing/back-and-forth mechanism 400 includes a positioning plate 401. The positioning plate 401 is fixed on the pitching frame 303. A yawing block 402 is provided above the positioning plate 401 so that the yawing block 402 is rotatable about the yawing axis 90 but immovable in the direction of yawing axis 90, relative to the positioning plate 401. A yawing shaft 403 extends along the yawing axis 90 (third axis) and vertically through the yawing block 402 so as to rotate about the yawing axis 90 together with the yawing block 402 relative to the positioning plate 401.

In the embodiment, as shown in FIG. 11, the yawing axis 90 (third axis) intersects with the pitching axis (second axis) 320 at, or substantially at, a right angle. The yawing axis 90 is positioned between two arms 301 of the pitching mechanism 300 and crosses or substantially crosses the rolling axis 220 (first axis).

A cylindrical scale support block 404, which is mounted around the yawing shaft 403, is provided above the yawing block 402. The scale support block 404 supports a scale plate 405 (a part of the indicator) which indicates the yawing angle. Corresponding to the scale plate 405, a scale index part 406 (a part of the indicator) is provided on the yawing block 402. In the embodiment, by using the indicator including the scale plate 405 and the scale index part 406, the angle of the yawing block 402, i.e., the yawing angle of the coil unit 20, can be confirmed or set by reading the scale plate 405 value pointed by the scale index part 406.

A number of holes 407 are formed on the top surface of the positioning plate 401 at a regular interval (for example, 15 degrees) on a circle centering on the yawing shaft 403 so that the yawing block 402 and also the yawing angle of the coil unit 20 are immovably retained at respective angles with respect to the pitching frame 303. An indexing plunger 408 has a shaft (not shown) which is forced downward by a spring (not shown) to fit in one of the holes 407. This allows that the yawing movement of the yawing block 402 and the coil unit 20 can be prohibited by fitting the indexing plunger 408 in one of the holes 407. As above, the indexing plunger 408 and the holes 407 function as a braking and locking mechanism of the yawing mechanism. Although in the embodiment the cross section of the holes 407 is elliptic with its major and minor axes oriented in the radial and circumferential directions, respectively, with respect to the yawing axis 90, it may be a circle or a polygon. Although not mentioned in the description of the embodiment, another structure may be taken for adjusting the posture of the coil, which employs a rotational mechanism capable of rotating the coil unit about another two independent axes substantially orthogonal to the yawing axis.

As shown in FIG. 14, the yawing block 402 includes an upper projection 410 which extends in the direction away from the yawing shaft 403. The yawing block 402 has, below the upper projection 410, a lower projection 411 extending in parallel with the upper projection 410 and a vertical guide portion 412 connecting between the upper projection 410 and the lower projection 411. The upper projection 410 supports the support block 413 of the coil unit 20.

The support block 413 includes a horizontal connecting portion 415 which is provided below the pitching plate 303 and connected for rotation at the lower end of the yawing shaft 403 extending through the pitching plate 303, and the threaded shaft 416 which connects the horizontal connecting portion 415 with the upper projection 410. The threaded shaft 416 is connected to a guided portion 417 including a nut (not shown) in which the threaded shaft 416 is engaged. As illustrated, the guided portion 417 includes a vertical surface 418 which is guided by the lower projection 411 of the yawing block 402, and upper and lower projections 419 and 420 projecting from the top and bottom ends of the vertical surface 418 toward the yawing block 402, respectively. In the embodiment, a distance between the upper and lower projections 410 and 411 on the yawing block 402 is determined to be equal to a distance between the upper and lower projections 419 and 420 in the guided portion 417. Thus, the support block 413 and the coil unit 20 can elevate along the yawing shaft 403 by the distance between the upper projection portions 410 and 419 and the lower projection portions 411 and 420, causing the coil unit 20 to move in the direction along the yawing axis 90 to adjust the distance between the coil unit 20 and the patient's head adjustable.

The threaded shaft 416 connecting between the support block 413 and the horizontal connecting portion 415 includes a threaded shaft mechanism (not shown) with a threaded shaft and a nut in which the threaded shaft engages. The threaded shaft of the threaded shaft mechanism is connected to a knob 422 mounted on the upper projection 410 so that the threaded shaft 416 is rotated by rotating the knob 422 to elevate the support block 413 relative to the yawing block 402. Although not described in detail, the threaded shaft mechanism has a slot which is formed at the top end of the threaded shaft 416 and extends transversely through the threaded shaft 416. The knob 422 has an engaging portion which movably fits the slot, so that the rotation by the knob 422 is transmitted to the threaded shaft through the engaging portion, which causes the threaded shaft to move in the axial direction relative to the engaging portion.

In order to indicate the height of the coil unit 20 with respect to the patient's head, the knob 422 is connected to the indicator 423, which allows that the coil unit 20 is set at a desired height with respect to the patient's head while reading the height indicated by the indicator 423. Preferably, a locking mechanism 424 is provided to prevent the free rotations of the knob 422 and the threaded shaft. Optionally, for example, a pair of stops 425 are provided for the pitching frame 303 to delimit the yawing range of the coil unit 20 (i.e., yawing range of the support block 413 relative to the yawing block 402).

5. Patient Positioning Mechanism

In the embodiment, the system includes three patient positioning mechanisms: first positioning mechanisms 500, second positioning mechanism 600, and third positioning mechanism 700. The first positioning mechanism 500 is to have the patient take a proper position by using a marking provided on his or her skin. The second positioning mechanism 600 is to position the patient by supporting the head of the patient sitting on the chair from behind. The third positioning mechanism 700 is to support the jaw of the patient sitting on the chair from below. Preferably, each of the first to third positioning mechanisms includes a locking mechanism for locking the movable members and the position indicating mechanism. The locking mechanism helps maintaining the position of the patient during treatment, and the position indicating mechanism reproduces the patient's position easily. Optionally, a braking mechanism may be provided for braking the movements of the members.

5-1. First Positioning Mechanism 500

Figure 15:
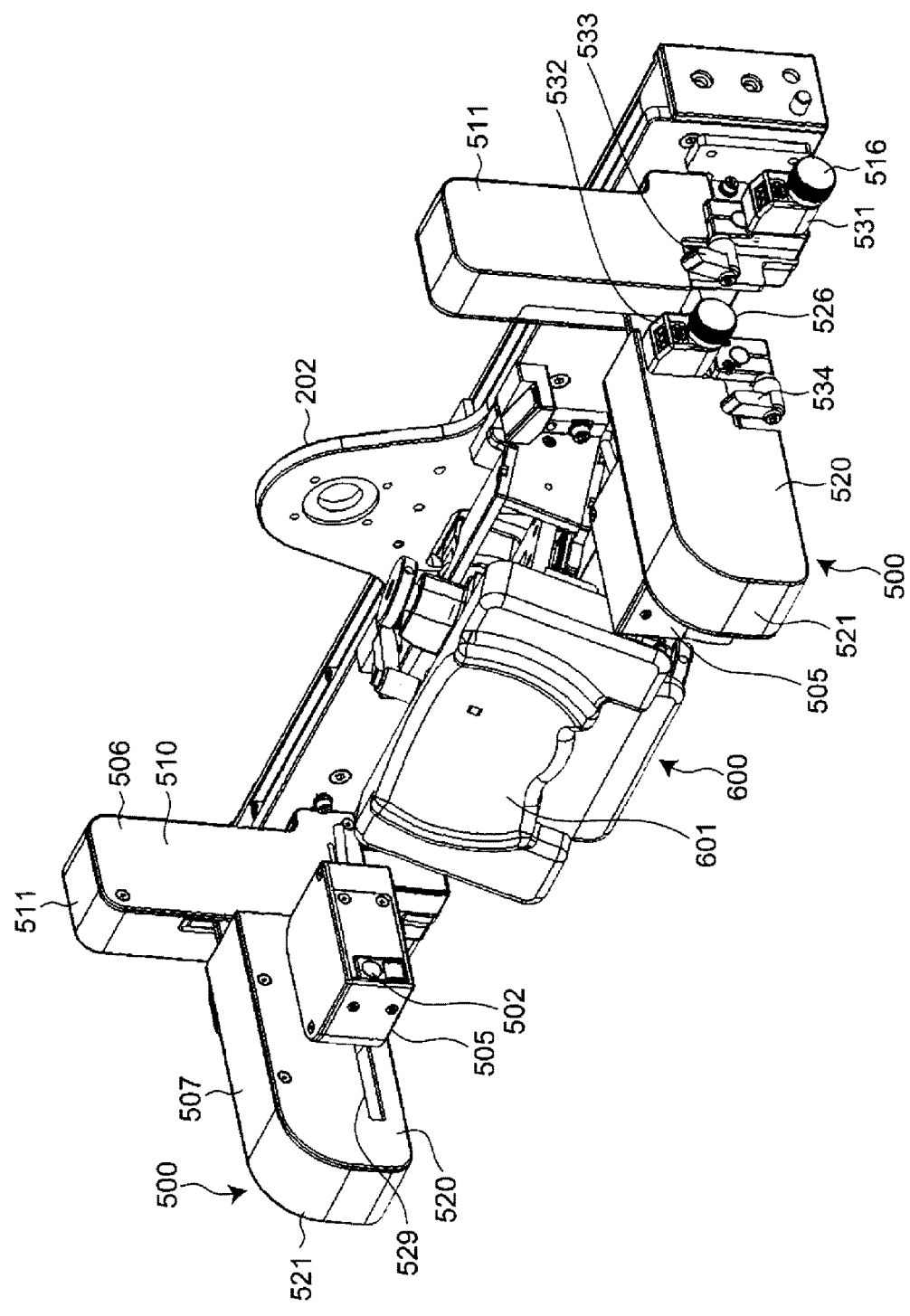
FIG. 15 is a perspective view showing the first positioning mechanism of the transcranial magnetic stimulation system in FIG. 1.
Figure 16:
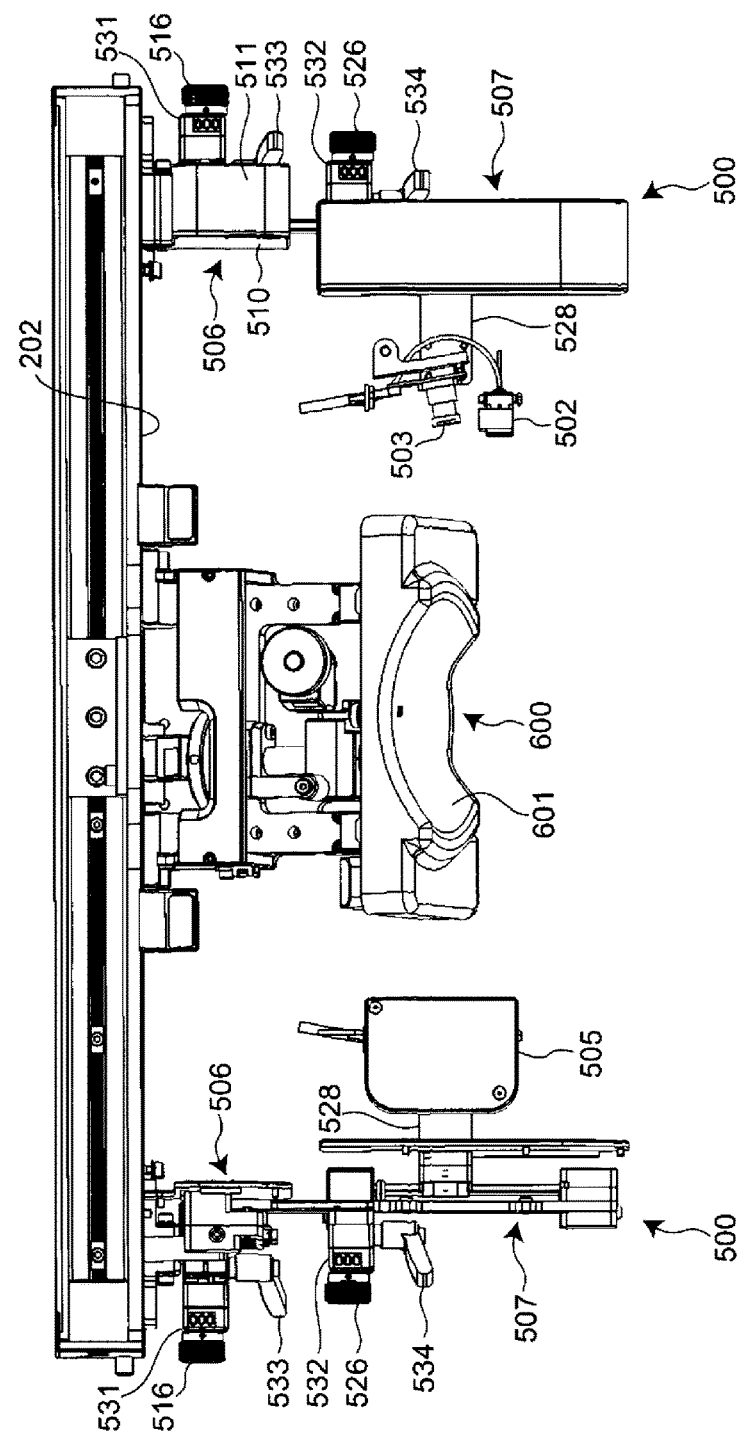
FIG. 16 is a plan view showing the first positioning mechanism of the transcranial magnetic stimulation system in FIG. 1.
Figure 17:
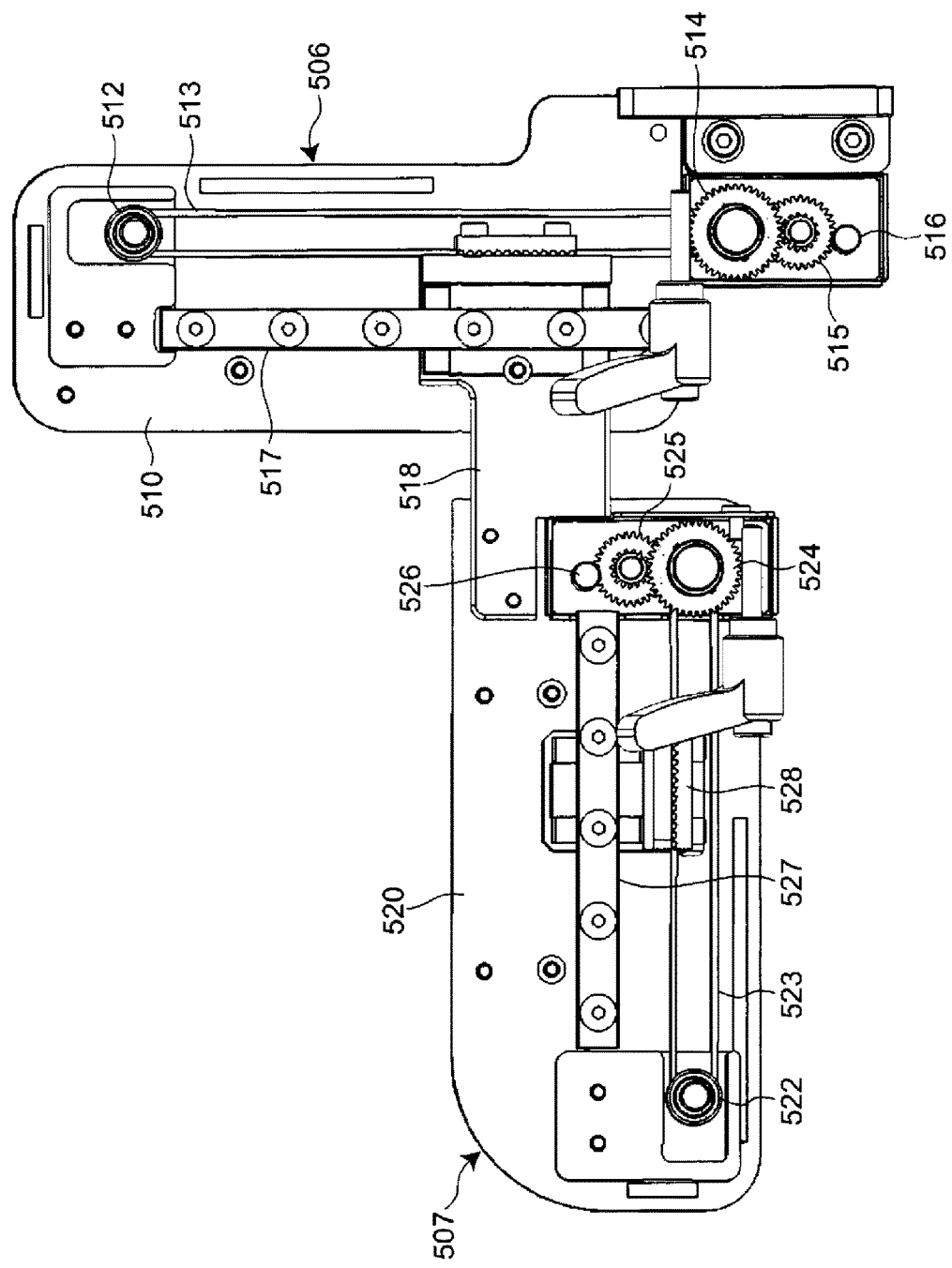
FIG. 17 is a side view showing the first positioning mechanism of the transcranial magnetic stimulation system in FIG. 1.

Referring to FIGS. 15-17, the first positioning mechanisms 500 are securely attached to left and right sides of the fixed frame 202. Each of the first positioning mechanisms 500 includes a light emitting unit (light emitter) for transmitting light toward the side surface portion of the patient's head (e.g., a marking (specific point) 800 (see FIG. 22) attached behind the earlobe of the patient), and a sensor 502 having a light receiving unit (light receiver) for detecting the light reflected from the marking, and the camera 503 (see FIG. 16) for taking pictures of the marking and the light spot on the marking. In FIG. 15-17 the positioning mechanism 500 is attached to the fixed frame 202. This is a specific embodiment of the invention and the positioning mechanism 500 may be attached to the horizontally or vertically moving parts in a second positioning mechanism 600 described below.

Figure 23:
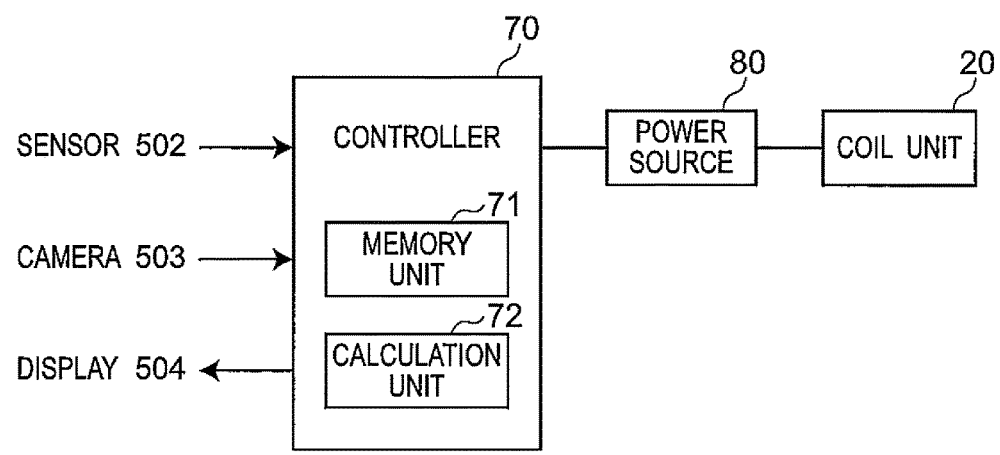
FIG. 23 is a control block diagram of the transcranial magnetic stimulation system in FIG. 1.

As shown in FIG. 23, the sensor 502 and the camera 503 are electrically connected to the controller 70. The controller 70 is electrically connected to the display 504 fixed to the chair 30 so that the optical information detected by the sensor 502 and the image acquired by the camera 503 may be indicated on the display 504.

The sensor 502 may be either a color sensor or a light quantity sensor. The color sensor includes a light emitter for emitting three components of light (RGB), an optical system for directing the light from the light emitter in a predetermined direction and redirecting the reflected light coming back from the direction toward the light receiver, and a color sensor for detecting a ratio among the three color components of the light received by the photodetector. A light quantity sensor includes a light receiver, an optical system for directing the light from the light emitter in a predetermined direction and redirecting the reflected light coming back from the direction toward the light receiver, and a light intensity sensor for detecting the intensity of the light received by the light receiver.

Referring back to FIGS. 15 and 16, the sensor 502 and the camera 503 are accommodated in the casing 505 with their optical axes oriented toward the patient. The light axes of the sensor 502 and the camera 503 may not be in parallel to each other. As shown, the casing 505 is arranged so that the sensor 502 and the camera 503 face toward the marking on the head of the patient sitting on the chair 30. As is shown clearly in FIG. 1, the sensor 502 and the camera 503 are supported by two moving mechanisms 506 and 507 which move the sensor 502 and the camera 503 in a quasi-horizontal direction (back and forth direction) which is tilted up at about 15 degrees in the rear-to-front direction with respect to the horizontal direction and also in a quasi-vertical direction which is vertical to the quasi-horizontal direction. Although, the quasi-horizontal direction is not the true horizontal direction and the quasi-vertical direction is not the true vertical directions, for convenience in the following descriptions relating to the first positioning mechanism 500 the quasi-horizontal direction and the quasi-vertical direction will be called as "the horizontal direction" and "the vertical direction", respectively, and also the mechanisms for moving in the quasi-horizontal and in the quasi-vertical directions will be called as "horizontal moving mechanism" and "vertical moving mechanism", respectively.

The vertical moving mechanism 506 includes an elongate base plate 510 extending in the vertical direction and a cover 511 for protecting the mechanism (described below)

arranged on the base plate 510. An upper pulley 512 and a lower pulley (not shown) are provided at the upper and lower portions of the back surface of the base plate (the surface away from the patient), and an endless belt 513 is entrained around the pulleys 512. The shaft supporting the lower pulley (not shown) also supports a gear 514. The gear 514 is coupled to a manipulating knob 516 through one or more adjacent gears 515 so that the belt 513 moves in either direction by rotating the manipulating knob 516. The base plate 510 also supports a guide portion 517 extending parallel to the belt 513 and a connection member 518 capable of moving up and down in the vertical direction along the guide portion 517. Also, the connection member 518 is connected to the belt 513.

The other end of the connection member 518 supports a horizontal moving mechanism 507. The horizontal moving mechanism 507 includes an elongate base plate 520 extending in the horizontal direction and a cover 521 for protecting the mechanism (described below) arranged on the base plate 520. The base plate 520 is attached to the connection member 518 at one back end thereof closer to the vertical moving mechanism 506. A front pulley 522 and a rear pulley (not shown) are provided on the front and rear portions of the back surface of the base plate, and an endless belt 523 is entrained on the pulleys 522. A shaft supporting the rear pulley (not shown) also supports a gear 524. The gear 524 is connected to a manipulating knob 526 through one or more adjacent gears 525 so that the belt 523 moves in either direction by rotating the manipulating knob 526. The base plate 520 also supports a guide portion 527 extending parallel to the belt 523 and a carriage 528 capable of moving in horizontal direction along the guide portion 527. The base plate 520 has an opening 529 extending in the horizontal direction. A part of the carriage 528 extends through the opening 529 to appear on the opposite side of the base plate (facing the patient), to which the casing 505 is supported.

Thus, the casing 505 is moved in the horizontal direction (back and forth direction) by rotating the manipulation knob 526 of the horizontal moving mechanism 507 and is also moved in the vertical direction (up and down direction) by rotating the manipulation knob 516 of the vertical moving mechanism 506.

Preferably, indicators 531 and 532 are provided for the vertical and horizontal moving mechanisms 506 and 507 for indicating an angle of rotation of the knobs 516 and 526, respectively, so that the user can see or reproduce the vertical and horizontal positions of the casing 505. Also preferably, locking mechanisms 533 and 534 are provided to prohibit the free rotations of the knobs 516 and 526, or the gears 514, 515, 524 and 525 and thereby to hold the casing 505 in set position. Further preferably, the sensor 502 has a wide detection range that can accommodate an individual difference which may be caused due to the variation of patient's head sizes to prevent an occurrence of a condition in which a distance between the sensor and the marking would be greater than the detection range of the sensor.

5-2. Second Positioning Mechanism 600

Figure 18:
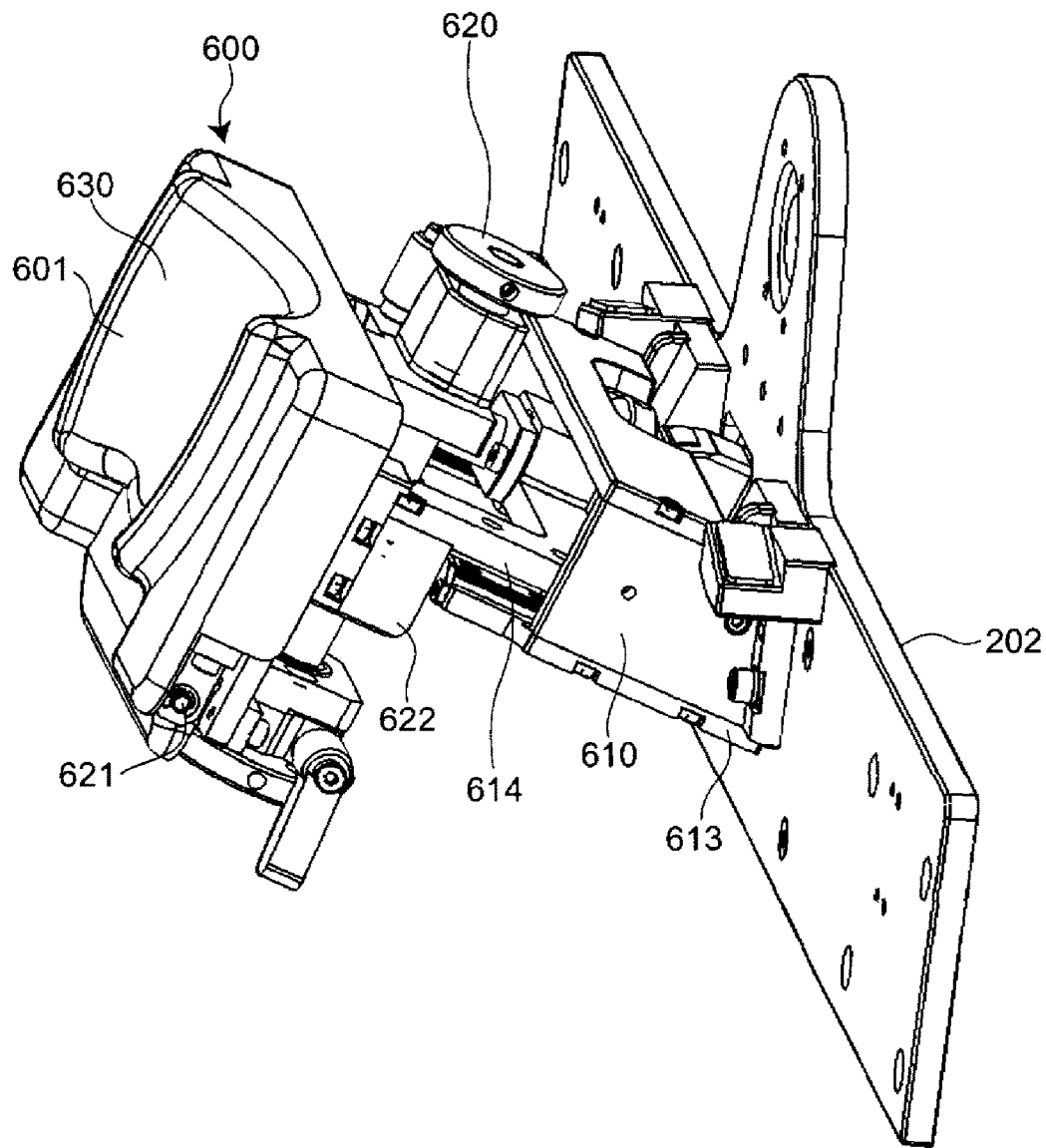
FIG. 18 is a perspective view showing the second positioning mechanism of the transcranial magnetic stimulation system in FIG. 1.
Figure 19:
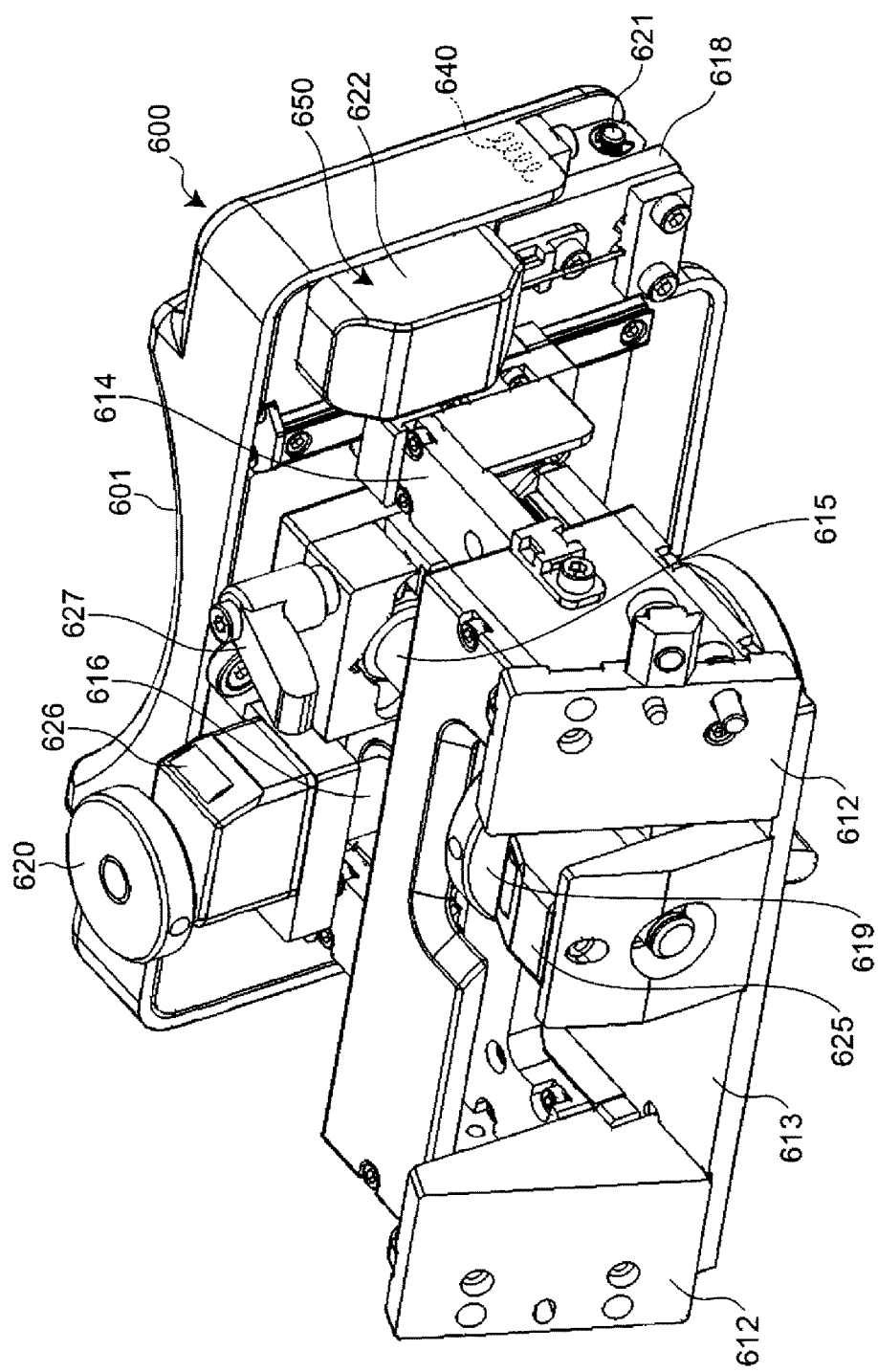
FIG. 19 is a perspective view showing the second positioning mechanism of the transcranial magnetic stimulation system in FIG. 1.
Figure 20:
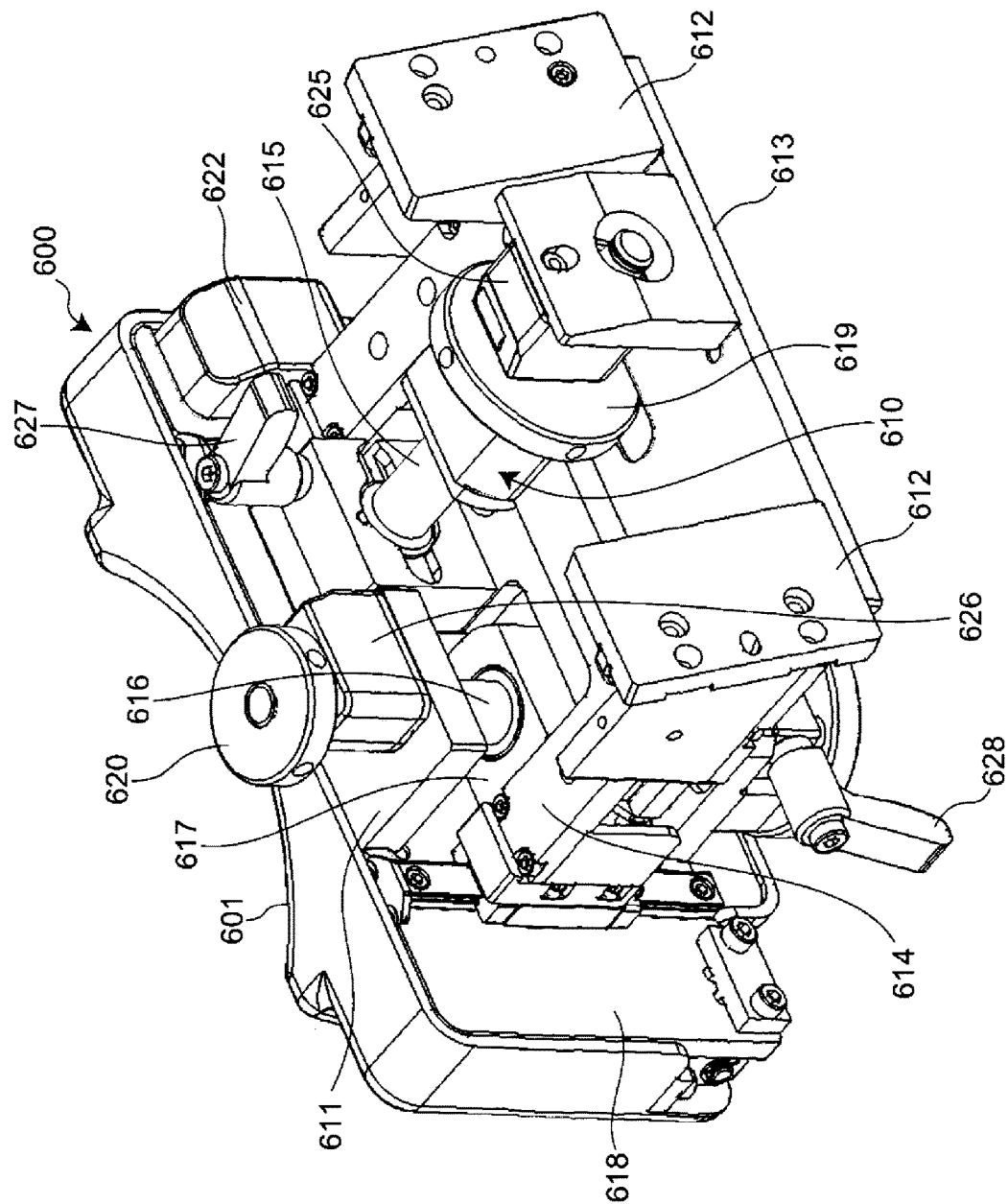
FIG. 20 is a perspective view showing the second positioning mechanism of the transcranial magnetic stimulation system in FIG. 1.

As shown in FIGS. 18-20, the second positioning mechanism 600, which is supported by the fixed frame 202 between two first positioning mechanisms 500, includes a headrest 601 for supporting the back of the patient's head sitting on the chair and two moving mechanisms 610 and 611 for moving the headrest in one direction which is upwardly tilted from rear to front at a certain angle (about 15 degrees, for example) and also in another direction which is orthogonal to the one direction. Although the one and the other directions are not the true horizontal and vertical directions, for convenience of description they will be called as "horizontal or back and forth direction" and "vertical direction" in the following descriptions relating to the second positioning mechanism 600. Hereinafter, the moving mechanisms for moving the headrest in the horizontal or back and forth direction and the vertical direction or up and down direction will be called as "horizontal moving mechanism" and "vertical moving mechanism", respectively.

The horizontal moving mechanism 610 includes brackets 612 fixed to the fixed frame 202 and a fixing block 613 fixed to the brackets 612. The fixing block 613 supports a horizontal moving block 614 so that the horizontal moving block 614 is capable of moving in horizontal or back and forth direction. The fixing block 613 and the horizontal moving block 614 are connected to each other by a threaded shaft 615 which extends in the horizontal or back and forth direction so that the horizontal moving block 614 moves in the back and forth direction with respect to the fixing block 613 according to the rotation of the horizontal threaded shaft 615. The horizontal moving block 614 is connected to a vertical moving block 617 through a threaded shaft 616 which extends in the vertical direction. The vertical moving block 617 supports a base plate 618 which is arranged behind the headrest 601. Thus, the headrest 601 moves back and forth in the horizontal or back and forth direction by rotating the horizontal threaded shaft 615 or the knob 619 fixed thereto. Also, the headrest 601 moves back and forth in the vertical direction by rotating the vertical threaded shaft 616 or the knob 620 fixed thereto.

The headrest 601 is provided so as to make a pivotal movement within a certain angle between the forward and rearward positions. In this embodiment, the support mechanism includes a horizontal shaft 621 (see FIGS. 18 and 19) provided at a lower portion of the base plate 618 to extend in the left and right direction, on which the headrest 601 is supported for pivotal movement. In the embodiment, the headrest 601 is urged forward by an urging mechanism (for example, a spring) 640 (see FIG. 19) provided between the headrest 601 and the base plate 618. The base plate 618 also has a head detection mechanism 650 which detects whether the headrest 601 is forced in the rearward position due to the contact with the patient's head.

In this embodiment, the head detection mechanism 650 includes a detection means as a switch 622, for example, in order to detect by using an output of the switch 622 whether the headrest 601 takes the forward position due to the force from the spring 640 or takes the rearward position against the force from the spring 640. The head detection mechanism is not limited to the one with the switch, as long as it can detect the headrest 601 taking its forward or rearward position. The head detection mechanism is not limited to the one which detects the headrest 601 in the forward position due to the force of spring or in the rearward position against the force of spring. For example, the head detection mechanism may be the one in which a switch or optical or pressure sensor is provided in the headrest 601 for detecting whether the back portion of patient's head is in contact with the headrest 601. Also, the head detection mechanism may be provided in another head supporting mechanism other than the headrest, such as a mechanism supporting a patient's chin (for example, mechanism including chinrest 703) or a mechanism supporting a patient's forehead.

The head support mechanism, which is provided for supporting the patient's head in place in a certain condition in which other mechanisms take respective operational positions, may include the headrest 601, chinrest 703, a portion of the coil casing 21 designed to make a contact with the patient's head, or a mechanism for supporting the patient's forehead. The head support mechanism allows the patient's head to be fixed in the treatment position. Preferably, the head support mechanism has a contour which is substantially similar to the contacting patient's head surface for easier support of the patient's head. For example, the headrest 601 preferably has a concaved shape close to the curvature of the back of the patient's head so that the back of the head fits in and well supported by the headrest 601. The head support mechanism may not necessarily be provided to a portion for supporting the patient's head, and it may be modified according to the embodiment. Of course, the head support mechanism may be provided only in the headrest 601.

Preferably, indicators 625 and 626 are provided on the threaded shafts 615 and 616 extending in the horizontal or back and forth direction and the vertical direction, respectively, in order to see or reset the horizontal and vertical positions of the headrest 601. Also preferably, locking mechanisms 627 and 628 are provided to the horizontal or back and forth moving mechanism 610 and the vertical moving mechanism 611 for maintaining the set position of the headrest 601 in the horizontal or back and forth direction to prevent the free rotation of the knobs 619 and 620 or the threaded shafts 615 and 616, respectively.

5-3. Third Positioning Mechanism 700

Figure 21:
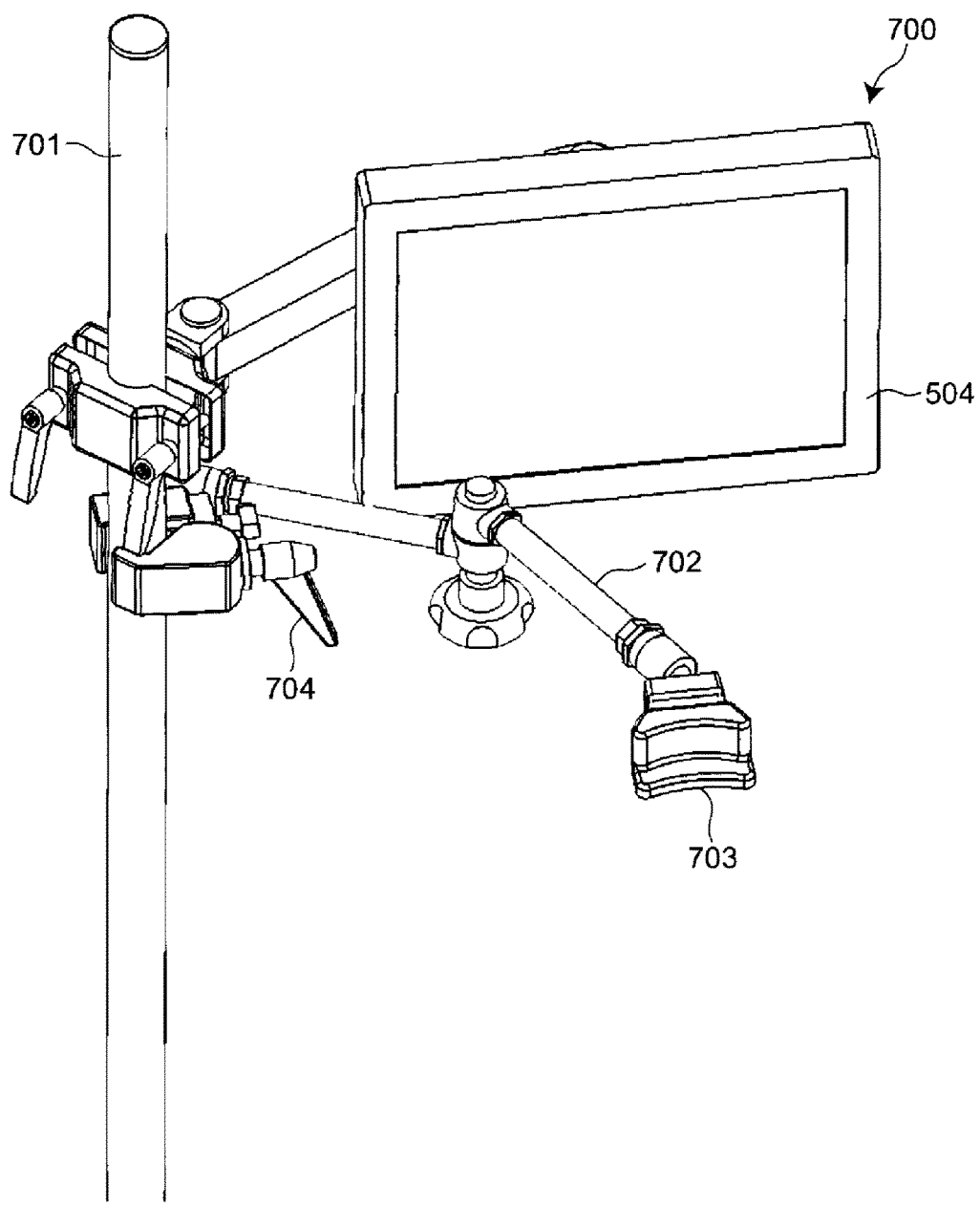
FIG. 21 is a perspective view showing the third positioning mechanism of the transcranial magnetic stimulation system in FIG. 1.

As shown in FIG. 21, the third positioning mechanism 700, which is to support the chin of the patient sitting on the chair 30, includes a post or column 701 fixed on the chair 30, a horizontal arm 702 connected to the post 701, and the chinrest 703 attached at the distal end of the horizontal arm 702. Although the horizontal arm 702 is made of two arm elements connected so that they can pivot relative to each other and be fixed to each other in the embodiment, it may be made of single element or may be made of three or more elements. The horizontal arm 702 and the chinrest 703 supported by the horizontal arm 702 may be designed to be secured to the post 701 by a locking mechanism 704, for example. Using the third positioning mechanism 700 so constructed, the head of the patient sitting on the chair 30 is well restricted and thereby supported by the headrest 601, chinrest 703, and the coil unit 20 from respective directions (from behind, below, and above).

6. Operation

The operation of the system 10 so constructed will be described below.

6-1. Determination of Optimum Stimulation Point

The optimum condition of the system 10 most suitable for the treatment of the patient (including, for example, the height of the coil unit, position in the left and right direction (rolling angle), and position in the back and forth direction (pitching angle), yawing angle, and distance with respect to the patient) is set. The system condition setting is performed by moving or rotating the coil unit 20 relative to the patient sitting in the chair to determine a position in which the most effective magnetic stimulation is given to the target position.

Specifically, in the system condition setting, the lower carriage 102 of the elevating mechanism 100 is fixed at the expected optimum height or at a height slightly above the optimum height. If necessary, the upper carriage 103 supporting the mounting unit 50 may be separated from the lower carriage 102 and retained in an elevated position. The display 504 connected to the post 701 and the third positioning mechanism 700 with the chinrest 703 thereof is moved out of the patient approaching way to let him or her sit into the chair 30.

Next, the mechanisms described above are adjusted. Those mechanisms may be adjusted independently, rather than in a predetermined order. For example, the elevation mechanism 100 is operated to adjust the height of the mounting unit 50. Then, the second positioning mechanism 600 is operated to adjust the height and the position of the headrest 601 in the back and forth direction. Also, the rolling mechanism 200, the pitching mechanism 300, and the yawing/moving mechanism 400 are operated to adjust the position of the coil unit 20. Typically, at this point the patient-facing surface of the casing including the coil 22 in the coil unit 20 is substantially in contact with the surface of the patient's head. This allows that the patient's head is supported from back by the headrest 601 and also supported from above by the coil unit 20 to take a stable position. As described above, the coil unit 20 and the headrest 601 define a specific space for accommodating the patient head with specific configuration and position, which results in a stable positioning against the patient's stimulation point. If necessary, the patient's chin may be supported from below by the chinrest 703. This results in that the patient's head is supported by the third positioning mechanism 700 at three points, i.e., the headrest 601, coil unit 20, and chinrest 703.

After completion of the above-described preparation, the coil unit 20 is turned on to apply the magnetic stimulation to the patient. In this operation, the optimum condition for the most effective application of the magnetic stimulation at the target point is determined by operating the elevation mechanism 100, rolling mechanism 200, pitching mechanism 300, yawing/moving mechanism 400, and/or second positioning mechanism 600 and, thereby, adjusting the height, position in the left and right direction (rolling angle), position in the back and forth direction (pitching angle), yawing angle, distance between the coil unit and the patient. If necessary, the chin of the patient is supported by the chinrest using the third positioning mechanism 700. Specifically, the coil unit 20 is moved around the target position to observe physiological reaction of the patient such as twitching, and a position where the physiological reaction is significantly observed is determined as the optimum position. This determination can be done without using a three-dimensional measuring system such as infrared stereo camera. If the twitching is not observed, an electromyography or three-dimensional measurement system may be used.

During the adjustment is being performed, the coil unit 20 is pivotally moved in the back and forth and left and right directions around the rolling axis 220, in back and forth direction around the pitching axis 320, rotated around the yawing axis 90, and moved to and away from the patient's head along the yawing axis 90, which ensures that the most suitable condition is determined for the patient. In this operation, the coil unit 20 is moved along the median and coronal planes. Also, the surface of the casing 23 moves along median and front-head surface planes of the average adult head, which ensures that the coil is retained as close to the patient's head as possible during the movement. Therefore, the adjustment of the rolling or pitching angle requires only a minimum re-adjustment of the yawing angle and/or the height of the coil unit.

In the embodiment, because three axes (rolling axis 220, pitching axis 320, yawing axis 90 in FIG. 11) defining movements of the coil 22 are positioned in a certain relationship to each other, the optimum position of the coil is readily determined. The optimum condition or position so determined can be recorded using the indications of the indicators. The indications of the indicators indicate not only respective positions of the moving elements or rotating elements supporting the indicators but also the position of the coil unit, namely, moving the moving elements or rotating the rotating element according to the indications of the indicators is to move or rotate the coil. Therefore, the subsequent treatment only needs the respective mechanisms to be adjusted simply by setting the indications of the indicators to respective values corresponding to the optimum condition or position, which means that each treatment does not need time consuming preparatory actions for determining the optimum condition. Also, an optimum condition for one patient may be obtained quickly and readily by using the optimum condition or conditions obtained for any other person or persons. The optimum conditions obtained in one facility such as hospital may be commonly used in the same or similar systems installed in any other facilities such as hospital and patient's house, which ensures the optimum coil condition to be reproduced in those systems without difficulty.

Figure 22:
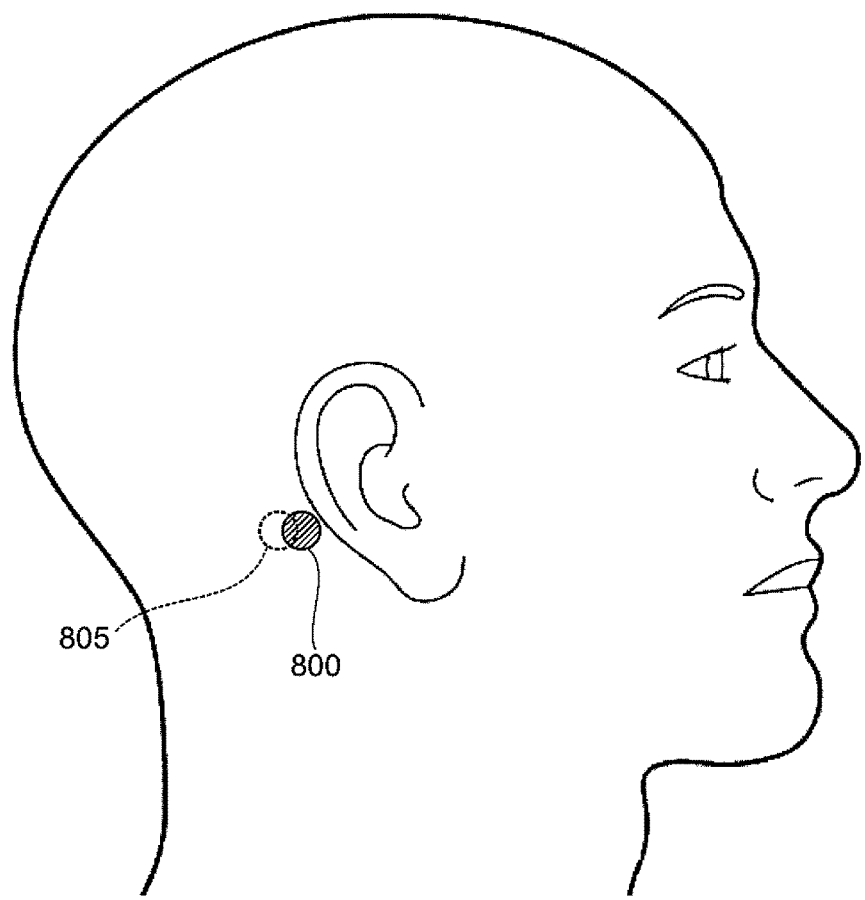
FIG. 22 is a diagram showing the marking on the patient and the light spot projected targeting the marking.

In order to ensure the reproducibility of the optimum condition, preferably the patient is guided into the same predetermined position of the optimally adjusted system 10, by using the first positioning mechanism 500. To this end, as a preparation, light transmitted from the sensor 502 of the first positioning mechanism 500 is projected to the patient sitting on the chair 30 of the system 10 in which the elevation mechanism 100, rolling mechanism 200, pitching mechanism 300, yawing/moving mechanism 400, and the second positioning mechanism 600 have been all optimized. Preferably, the light projected position is a patient's portion which is less subject to move with the movements of the skin of patient's face skin, such as portions behind left and right ear lobes of the patient as shown in FIG. 22. Then, a marking 800 is provided on the portions where the light is projected. The marking 800 has the same size and shape as or different size and shape from that of light spot 805 so that the light spot 805 overlaps the marking 800. The marking may be made on the patient's skin by using a marking pencil, art-making, or attaching a suitable patch.

Once the marking 800 is made, the sensor 502 is energized to project light toward the marking on the patient. When the light spot 805 and the marking 800 are in best alignment with each other, the sensor detects the reflected light to memorize information (reference information) contained in the reflected light. The reference information is not limited to that obtained when the marking 800 and the light spot 805 are in best alignment, and it may be defined by using reflected light which is misaligned with the marking to the extent harmless to the treatment. If the sensor 502 is made of a color sensor, the memorized reference information is the information of RGB component ratio. If the sensor is the light intensity sensor, the memorized reference information is the information of light intensity. In the embodiment, the reference information is memorized in a memory unit (memory means) 71 of the controller 70 described below (see FIGS. 2 and 3) and is used as a reference (reference RGB ratio, reference light intensity) in a guide control which will be described below. The memory unit 71 also reads and memorizes the indications of the indicators 531 and 532 of the first positioning mechanism 500. If the sensor 502 has a memory, the reference information may be memorized in this memory.

Preferably, either or both of the left and right markings 800 are provided at respective positions rearwardly away from a vertical central line of the head when viewed from its side in order to reproduce the position of the patient's head precisely. The number of the markings provided on each side is not limited to one, and two or more markings may be provided on each side. In the latter case, the alignment may become more complicated, but improving an accuracy of the alignment can contribute to the precise positioning.

As described above, the patient positioning mechanisms 500, 600 and 700 provide an good guidance for the patient into the mounting unit 50, which contributes to a proper positioning of the patient against the coil.

6-2. Magnetic Stimulation Treatment

For the second and subsequent magnetic stimulation treatments, the system 10 is set into the optimum condition obtained during the system condition setting (first treatment) described above. For the optimum setting, the elevation mechanism 100, the rolling mechanism 200, the pitching mechanism 300, the yawing/moving mechanism 400, the first positioning mechanism 500, and the second positioning mechanism 600 are all adjusted so that the indicators associated thereto show the respective optimum indications. As above, the position indicating mechanisms (indicators) allow the coil to be repeatedly positioned at the optimum stimulation position readily and with good reproducibility. Thus, using the electromyography or the three-dimensional measurement system may not be needed.

The mechanisms may be adjusted in any order. Preferably, first the adjustment mechanisms 100, 200, 300, and 400 are adjusted according to the optimum condition obtained by the system condition setting to place the coil at the optimum position, second the patient positioning mechanisms 500, 600, 700 are adjusted to let patient sit on the chair, and finally the position of the patient is adjusted.

The first positioning mechanism 500 for guiding the patient into the proper position directs the light emitted from the light emitters of the first positioning mechanism 500 to the patient as shown in FIG. 22. If the posture of the patient is different from the posture from which the reference RGB ratio or the reference light intensity is obtained (for example, namely, the patient head is tilted to the left or right and/or up or down), the entire part or the substantial part of light spot 805 on the patient does not overlap the marking 800, which results in that the RGB ratio or the light intensity from the sensor 502 is different from the reference value.

Figure 24:
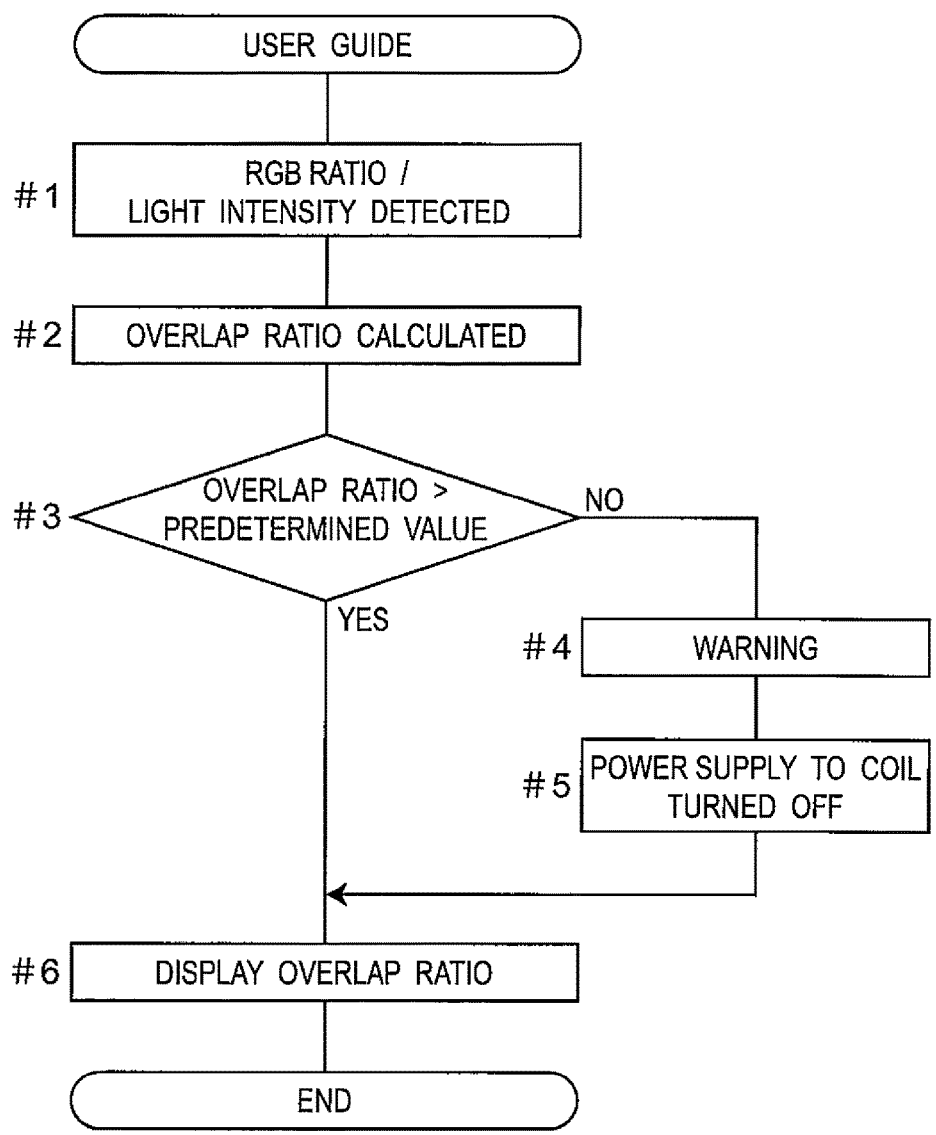
FIG. 24 is a diagram showing the control sequence of the transcranial magnetic stimulation system in FIG. 1.
Figure 25:
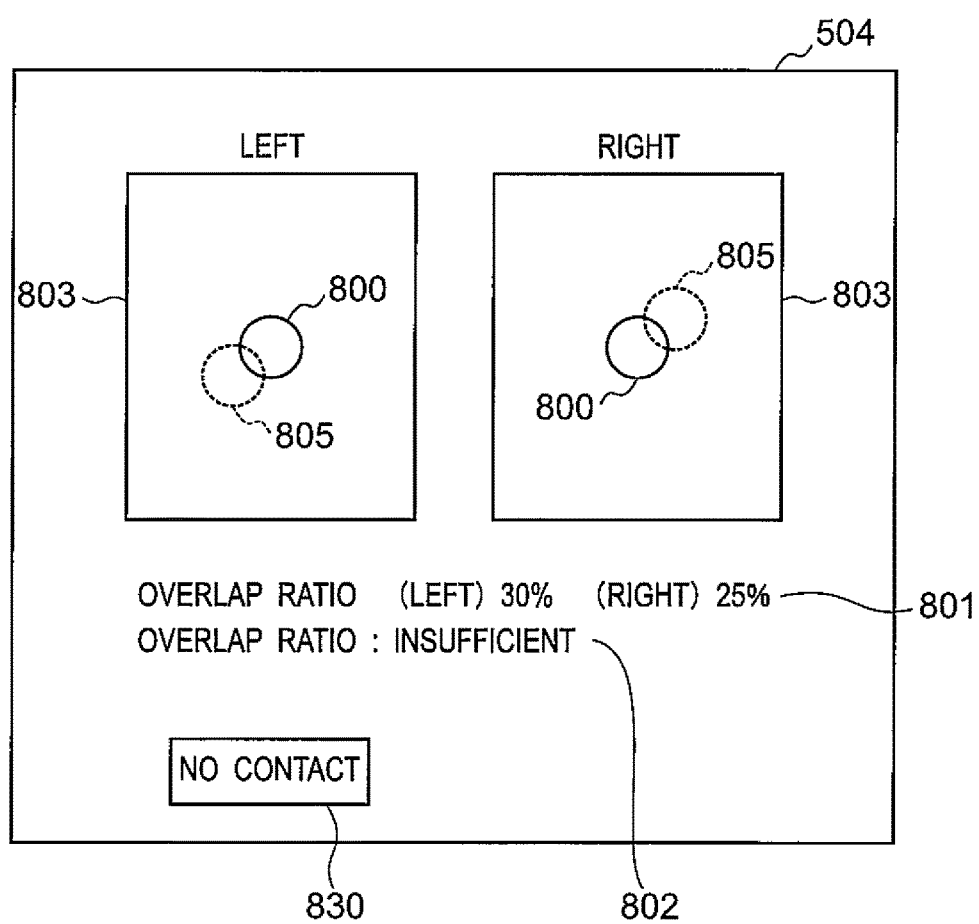
FIG. 25 is a diagram showing the display in the transcranial magnetic stimulation system in FIG. 1.

As shown in FIG. 24, the sensor 502 receives the light reflected from the patient and reads the information (comparison information) contained in the light, i.e., either the RGB ratio or the light intensity, and sends a corresponding signal to the controller 70 (step #1). The controller 70 calculates the overlap ratio between the marking 800 and the light spot 805, using the signal received by the sensor 502 (comparison information) at the calculation unit 72 of the controller 70 (step #2). The overlap ratio may be indicated in the form of RGB ratio or the light intensity in the reflected light (comparison value) to the reference RGB ratio or the reference light intensity (reference value). In the embodiment in which the sensor 502 has a calculation unit, the calculation unit of the sensor 502 may also calculate the overlap ratio. If the light spot insufficiently overlaps the marking and then the overlap ratio is equal to or less than a predetermined value (threshold), the display 504 shows a warning 802 indicating that the overlap ratio is insufficient (steps #3 and #4). Simultaneously with or a certain period of time has elapsed after displaying the warning 802, a power supply to the coil 22 from the power source 80 may be turned off (step #5). Optionally, the overlap ratio 801 may be displayed (step #6).

The amount of the light reflected by the marking 800 varies depending on the material of the marking. More specifically, if the reflectivity of the marking is higher than that of the patient's skin, the light intensity becomes smaller as the overlap ratio between the marking 800 and the light spot 805 becomes smaller. In contrast, if the reflectivity of the marking is lower than that of the patient's skin, the light intensity becomes larger as the overlap ratio between the marking 800 and the light spot 805 becomes smaller. Therefore, using a material with higher reflectivity than that of the skin increases the light intensity in proportion to the overlap ratio. Also, if a material with lower reflectivity than that of the skin is used, the light intensity decreases in inverse proportion of the overlap ratio. Therefore, if the overlap ratio is calculated using the output from the light intensity sensor, preferably the aforementioned relationship between the overlap ratio and the light intensity should be taken into consideration.

The warning 802 may be a displayed message or may be a flashing image. In addition to or instead of displaying message or warning on the display 504, a sound or vibration warning may be provided. If the overlap ratio is above the predetermined value, namely, when the light spot substantially overlaps the marking, no warning is displayed. Instead, the overlap ratio 801 may be indicated on the display 504, or a specific image may be blinked or audio sound different from the warning may be used to notify the patient and/or the operator (step #4).

Preferably, both left and right images 803 taken by the cameras 503 are also displayed on the display 504. The patient can move his or her head into a proper portion by himself or herself by moving his or her head left and right and up and down while viewing the markings and light spots 805 indicated on the display 504.

As described above, the patient can repeatedly be set into the optimum treatment position against the system. If the patient moves his or her head during the treatment and, as a result, the overlap ratio falls below the predetermined value, a warning is issued in the form of display message on the display or sound. In this instance, the patient may move his or her head to the optimum treatment position by himself or herself while watching the display on the display 504. If it is detected before starting the treatment that the overlap ratio is below the threshold, the power supply to the coil 21 be is prohibited. Also, the power supply to the coil is halted during the treatment if the overlap ratio falls below the threshold due to the unintended movement of the patient. The movement of the patient can be seen on the display, which allows the patient to recover the optimum overlap ratio in light of the images on the display.

If patient's head moves off the headrest 601, the headrest 601 moves forward to change the state of the switch 622 mounted behind the headrest 601. Therefore, the forward movement of the headrest 601 beyond a predetermined distance, i.e., the fact that the patient's head has moved away from the proper position with respect to the headrest 601, may be detected by using the output of the switch 622 and, in this instance, the controller 70 can shut down the power supply to the coil unit 20 to terminate the magnetic stimulation. A warning means is provided in order to notify that the patient's head has moved off the headrest, in the form of sound, vibration, light, or image. For example, a message 830 such as "No Contact" may be indicated on the display 504. A sensing device such as an optical sensor or a pressure sensor may be provided at a proper location on the mounting unit 50, which allows that the contact of the patient's head with the headrest 601 is detected by using the output of sensing device.

In the preferred embodiment of the invention, the mounting unit 50 may be quickly moved away by the elevation mechanism 100. Also, no mechanism restricts the movement of the patient. This ensures that the patient can be removed from the system easily and quickly in case of trouble or emergency during the treatment.

Although discussions have been made to the preferred embodiments of the invention, the indicator in each mechanism may be a digital indicator or an analog indicator. The indicator may include a scale as described in the embodiments. Also, a mechanism such as such an angle meter, a position indicator, a linear encoder, or a potentiometer may be provided to indicate positional information. The indicator is intended to be used to indicate the optimum position of the coil unit and, therefore, any indicator may be used as long as it meets this intention. In particular, because the indicator directly indicates the precise position of the moving mechanism, it is useful in reproducing respective positions of the moving mechanisms in the whole system. According to the invention, no complicated control is necessary compared to the robotic device because the moving mechanisms according to the invention are operated manually. Meanwhile, a part of or the entire of the moving mechanisms may be designed to be driven electrically or automatically in part or as a whole

7. Other Embodiments

Various modifications may be made to the embodiments described above.

Although in the above descriptions the system is configured so that the overlap ratio is compared with one predetermined value (threshold) and then the conditions of the system are changed in accordance with the comparison result, the system may use two or more predetermined values (lower threshold and upper threshold). In this instance, when the overlap ratio is above the lower threshold and below the upper threshold, the warning is displayed and also a power supply to the coil is turned off simultaneously with the warning or a predetermined time period after making the warning. Alternatively, the system is configured so that, when the overlap ratio is above the lower threshold and below the upper threshold, the warning is displayed and the power supply is turned off a predetermined time period after making the warning and, when the overlap ratio is below the lower threshold, the warning is made and the power supply to the turned off simultaneously with the warning.

Although in the previous embodiment the first positioning mechanism 500 and the second positioning mechanism 600 are mounted on the housing 40, either or both of them may be mounted on the chair 30. In this embodiment, the patient is first positioned in place and then the chair is positioned to the properly positioned patient.

Also, although in the previous embodiment the coil is positioned to the patient sitting on the chair, the mechanism to support the patient is not limited to the chair and may be other mechanism such as a bed or the like.

Further, although in the previous embodiment above the system incorporates the coil position adjustment mechanisms (100, 200, 300, 400) and the patient position adjustment mechanisms (500, 600, 700), the coil position adjustment mechanisms may be replaced by other similar mechanism or mechanisms and/or the patient position adjustment mechanisms may be replaced by other similar mechanism or mechanisms, or either or both may be removed from the system provided that the coil can be set into the optimum position against the patient head.

Although discussions have been made to the specific first to fifth embodiments, each of which may be modified in various ways. For example, the first mechanism includes each and every mechanism configured to move the coil in the left and right direction about the first axis (rolling axis) extending in the back and forth direction of the patient's head, relative to the patient's head supported by the support mechanism 30. Likewise, the second mechanism includes each and every mechanism configured to move the coil in the back and forth direction about the second axis (pitching axis) extending in the left and right direction of the patient's head, relative to the patient's head supported by the support mechanism. Also, the third mechanism includes each and every mechanism configured to rotate the coil about the third axis extending radially from the first axis. Further, the fourth mechanism includes each and every mechanism configured to move the coil along the third axis. Furthermore, the fifth mechanism includes each and every mechanism configured to move the first mechanism toward and away from the patient.

The invention claimed is:

1. A transcranial magnetic stimulation system comprising:
   a sensor configured to project a light spot to a head of a patient and detect a reflection light of the light spot;
   a memory configured to store information included in the reflection light detected by the sensor as a reference information based on the light spot projected on the patient overlapping a marking provided on the patient;
   a controller configured to calculate an overlap ratio between the marking and the light spot based on the reference information stored in the memory and a comparison information included in the reflection light of the light spot; and
   a display configured to display the overlap ratio.

2. The transcranial magnetic stimulation system of claim 1, wherein each of the reference information and the comparison information includes a ratio of one or more light components included in the reflection light, respectively.

3. The transcranial magnetic stimulation system of claim 1, wherein each of the reference information and the comparison information includes an intensity of the reflection light, respectively.

4. The transcranial magnetic stimulation system in claim 1, further comprising a camera configured to capture images of the light spot projected on the head of the patient and the marking,
   wherein the display is further configured to display the images of the light spot and the marking that are captured by the camera.

5. The transcranial magnetic stimulation system in claim 1, wherein the controller is further configured to provide a warning based on the overlap ratio being below a predetermined value.

6. The transcranial magnetic stimulation system in claim 1, further comprising a magnetic stimulation coil,
   wherein the controller is further configured to stop a power supply to the magnetic stimulation coil based on the overlap ratio being below a predetermined value.

7. The transcranial magnetic stimulation system in claim 1, wherein the sensor is further configured to detect one or more markings provided on each of left and right sides of the head of the patient.

8. The transcranial magnetic stimulation system in claim 1, further comprising:
   a head support configured to support the head of the patient; and
   a sensing device configured to detect that the of the patient is in contact with the head support.

9. The transcranial magnetic stimulation system of claim 8, wherein the head support includes a headrest configured to support a back of the head of the patient.

10. The transcranial magnetic stimulation system of claim 9, further comprising:
    a support configured to support the headrest so that the headrest moves between an advanced position in which the headrest is advanced toward the head of the patient and a retracted position in which the headrest is retracted from the head of the patient; and
    a spring configured to force the headrest in a direction from the retracted position toward the advanced position.

11. The transcranial magnetic stimulation system in claim 9, wherein the headrest has a surface portion opposing the of the patient and having a shape corresponding to a surface of the head of the patient that is to be in contact with the headrest.

12. The transcranial magnetic stimulation system of claim 8, wherein the sensing device includes at least one from among a switch, an optical sensor, and a pressure sensor configured to detect whether the head of the patient is in contact with the head support, and
    the controller is further configured to provide a warning based on the sensing device detecting that the head of the patient is out of contact with the head support.

13. The transcranial magnetic stimulation system in claim 1, further comprising a chinrest configured to support a chin of the patient.

* * * * *